United States Patent [19]
Krebbers et al.

[11] Patent Number: 6,008,437
[45] Date of Patent: Dec. 28, 1999

[54] USE OF ANTHOCYANIN GENES TO MAINTAIN MALE STERILE PLANTS

[75] Inventors: Enno Krebbers, Houston, Tex.; Mark Williams, Ghent; Jan Leemans, Deurle, both of Belgium

[73] Assignee: Plant Genetic Systems, Brussels, Belgium

[21] Appl. No.: 08/750,357

[22] PCT Filed: Jun. 6, 1995

[86] PCT No.: PCT/EP95/02157

§ 371 Date: Mar. 21, 1997

§ 102(e) Date: Mar. 21, 1997

[87] PCT Pub. No.: WO95/34634

PCT Pub. Date: Dec. 21, 1995

[51] Int. Cl.$^6$ .............................. A01H 5/00; A01H 4/00; A01H 1/00; C12N 5/04
[52] U.S. Cl. .......................... 800/303; 800/271; 800/274; 800/320.1
[58] Field of Search ................................ 800/274, 320.1, 800/298, 300, 300.1, 302, 303, 271

[56] References Cited

U.S. PATENT DOCUMENTS

| | | |
|---|---|---|
| 3,842,538 | 10/1974 | Barabas . |
| 4,727,219 | 2/1988 | Brar et al. . |
| 5,356,799 | 10/1994 | Fabijanski et al. . |
| 5,525,716 | 6/1996 | Olsen et al. . |

FOREIGN PATENT DOCUMENTS

| | | |
|---|---|---|
| 198288 | 10/1986 | European Pat. Off. . |
| 344029 | 11/1989 | European Pat. Off. . |
| 412911 | 2/1991 | European Pat. Off. . |
| 91/02059 | 2/1991 | WIPO . |
| 92/09696 | 6/1992 | WIPO . |
| 93/25695 | 12/1993 | WIPO . |

OTHER PUBLICATIONS

*Nature*, "A Chimaeric Ribonuclease–Inhibitor Gene Restores Fertility to Male Sterile Plants", C. Mariani, et al., vol. 357, pp. 384–387, Jun. 4, 1992.

"The Mutants of Maize", M. Neuffer, et al., Published by the Crop Science Society of America, pp. 67–68.

"Breeding Field Crops", Third Edition, J. Poehlman, pp. 473–476.

V. Chandler, et al. "Two Regulatory Genes of the Maize Anthocyanin Pathway are Homologous: Isolation of B Utilizing R Genomic Sequences", *The Plant Cell* (1989) 1:1175–1183.

E. Coe, "Anthocyanin Genetics", *The Maze Handbook* (1994) pp. 279–281.

K. Cone et al., "Maize Anthocyanin Regulatory Gene pi is a Duplicate of c1 that Functions in the Plant", *The Plant Cell* (1993) 5:1795–1805.

G. Consonni et al., "Molecular Homology Among Members of the R Gene Family in Maize", *The Plant Journal* (1993)3:335–346, No. 2.

H. Dooner et al., "Genetic and Developmental Control of Anthocyanin Biosynthesis", *Annu. Rev. Genet* (1991) 25:173–99.

W. Galinat, "Use of Male–Sterile 1 Gene to Eliminate Detasseling in Production of Hybrid Seed of Bicolor Sweet Corn", *The Journal of Heredity* (1975) 66:387–388.

S. Goff et al., "Functional Analysis of the Transcriptional Activator Encoded by the Maize B Gene: Evidence for a Direct Functional Interaction Between Two Classes of Regulatory Proteins", *Genes & Development* (1992) 6:864–875.

S. Goff et al., "Identification of Functional Domains in the Maize Transcriptional Activator C1: Comparison of Wild–Type and Dominant Inhibitor Proteins", *Genes& Development* (1991) 5:298–309.

J. Goodrich et al., "A Common Gene Regulates Pigmentation Pattern in Diverse Plant Species", *Cell* (1992) 68:955–964.

Hartley, "Barnase and Barstar—Expression of Its Clones Inhibitor Permits Expression of a Cloned Ribonuclease", *J. Mol. Biol.* (1988) 202:913–915.

Ch. Jayaram et al., "Anthocyanin Pigmentation and Transposable Elements in Maize Aleurone", *Plant Breeding Reviews* (1990) 8:91–137.

K. Kaukis et al., "Sweet Corn Breeding", *Breeding Vegetable Crops* (1986) pp. 475–598.

T. Klein, "Regulation of Antocyanin Biosynthetic Genes Introduced into Intact Maize Tissues by Microprojectiles", *Proc. Natl. Acad. Sci.* (1989) 86:6681–6685.

S. Ludwig, "Lc, a Member of the Maize R Gene Family Responsible for Tissue–Specific Anthocyanin Production, Encodes a Protein Similar to Transcriptional Activators and Contains a myc–homology Region", *Proc. Natl. Acad. Sci.* (1989) 86:7092–7096.

(List continued on next page.)

*Primary Examiner*—Gary Benzion
*Attorney, Agent, or Firm*—Burns, Doane, Swecker & Mathis, LLP

[57] ABSTRACT

A plant consisting essentially of cells which comprise in their genome a homozygous male-sterility genotype at a first genetic locus; and a color-linked restorer genotype at a second genetic locus, which is heterozygous (Rf/–) for a foreign DNA Rf. The foreign DNA Rf comprises: a) a fertility-restorer gene capable of preventing the phenotypic expression of the male-sterility genotype, and b) at least one anthocyanin regulatory gene involved in the regulation of anthocyanin biosynthesis in cells of seeds of the plant which is capable of producing anthocyanin at least in the seeds of the plant, so that anthocyanin production in the seeds is visible externally. Preferably, the anthocyanin regulatory gene is a shortened R, B or C1 gene or a continuation thereof. The invention also relates to DNA sequences encoding shortened R, B or C1 anthocyanin regulatory genes and to a process for maintaining a line of male-sterile plants which comprises crossing a male-sterile parent plant and a maintainer parent plant comprising homozygous male-sterility genotype and a restore genotype comprising fertility-restorer gene and an anthocyanin regulatory gene.

65 Claims, 4 Drawing Sheets

OTHER PUBLICATIONS

J. Paz–Ares et al., "The Regulatory c1 Locus of *Zea mays* Encodes a Protein With Homology to myb Proto–oncogene Products and with Structural Similarities to Transcriptional Activators", *The EMBO Journal* (1987) 6:3553–3558, No. 12.

J. Paz–Ares et al. "Molecular Analysis of the C1–1 allele from *Zea mays*: a Dominant Mutant of the Regulatory C1 Locus", *The EMBO Journal* (1990) 9: 315–321, No. 2.

G. Perrot et al. "Nucleotide Sequence of the Maize R–S Gene", *Nucleic Acids Research* (1989) 17:8003, No. 19.

F. Quattrocchio et al., "Regulatory Genes Controlling Anthocyanin Pigmentation Are Functionally Conserved Among Plant Species and Have Distinct Sets of Target Genes", *The Plant Cell* (1993) 5: 1497–1512.

J. P. Radicella et al., "Cloning and Nucleotide Sequence of a cDNA encoding B–Peru, a Regulatory Protein of the Anthocyanin Pathway in Maize", *Plant Molecular Biology* (1991) 17:127–130.

J.P. Radicella et al., "Allelic Diversity of the Maize B Regulatory Gene: Different Leader and Promoter Sequences of two B Alleles Determine Distinct Tissue Specificities of Anthocyanin Production", *Genes & Development* (1992) 6:2152–2164.

B. Scheffler, "Molecular Analysis of C1 Alleles in *Zea mays* Defines Regions Involved in the Expression of This Regulatory Gene", *Mol. Gen. Genet* (1994) 242:40–48.

N. Stoskopf, "Plant Breeding: Theory and Practice"Westview Press, Chapter 22, pp. 453–472.

Mariani et al., "Induction of Male Sterility in Plants by a Chimaeric Ribonuclease Gene", *Nature* (1990) 347:737–741, No. 6295.

K. Cone et al., "Cloned Anthocyanin Genes and Their Regulation", *The Maize Handbook,* M. Freeling, V. Walbot eds. Springer Verlag, New York, Inc. pp. 282–285.

G. Consonni et al. "cDNA Nucleotide Sequence of Sn, a Regulatory Gene in Maize", *Nucleic Acids Research,* (1992) 20:373 No. 2.

S. Goff et al. "Transactivation of Anthocyanin Biosyntheic Genes Following Transfer of B Regulatory Genes into Maize Tissues", *EMBO Journal* (1990) 9:2517–2522, No. 8.

1. Transform a plant of line A with male-sterility gene S
   $A^{S/-}$

2. Transform a plant of line A with color-lined restorer gene Rf:
   $A^{rf/-}$

3. Cross the plants of 1 and 2

Progeny Table of $A^{S/-} \times A^{rf/-}$

|  | -, Rf | -,- |
   |---|---|---|
   | S,- |  | $A^{S/-, +/-}$ |
   | -,- | $A^{+/-, Rf/-}$ | $A^{+/-, +/-}$ |

4. Select the progeny from the cross of 3 with both the S and Rf genes (e.g. by means of PCR, or by presence of linked selectable genes)

FIGURE 1

5. Cross the $A^{S/-, Rf/-}$ plants from 4 with $A^{S/-,-}$

Progeny Table of $A^{S/-, Rf/-} \times A^{S/-,-}$

|  | S,- | -,- |
   |---|---|---|
   | S,Rf |  |  |
   | S,- | $A^{S/S,-/-}$ | $A^{S/-,-/-}$ |
   | -,Rf |  | $A^{-/-, Rf/-}$ |
   | -/- | $A^{S/-,-/-}$ | $A^{-/-,-/-}$ |

6. Select colored seeds, grow into plants and self all plants that contain both the S and rf genes (e.g. by means of PCR, or by presence of linked selectable marker genes).

Two possible progeny tables depending on the genotype of the selfed plant.

| Genotype of selfed plant | Genotype of progeny | Frequency of genotype in progeny | Color phenotype of progeny seeds | Male-fertility phenotype of progeny plants |
   |---|---|---|---|---|
   | S/-, Rf/- | genotypes as in progeny table in 5 | 75% / 25% | colored seeds / non-colored seeds | fertile / 75% fertile, 25% sterile |
   | S/-, Rf/- |  |  |  |  |

Progeny which display 75% colored and 25% non-colored seeds and in which all non-colored seeds grow into male sterile plants are retained.

FIGURE 1 (bis)

7. Cross the male-sterile plants of the retained progeny of 6 with the male-fertile plants of the retained progeny in 6.
   Analyze progeny of each cross. Two types of crosses are possible:
   1. S/S, Rf/Rf x S/S, -/-, or
   2. S/S, Rf/- x S/S, -/-

| Cross | Genotype of progeny | Frequency of genotype in progeny | Color phenotype of progeny seeds | Male-Fertility phenotype of progeny plants |
|---|---|---|---|---|
| S/S, Rf/Rf x S/S,-/- | S/S, Rf/- | 100% | colored seeds | fertile |
| S/S, Rf/- x S/S,-/- | S/S, Rf/- | 50% | colored seeds | fertile |
|  | S/S, -/- | 50% | non-colored seeds | sterile |

The progeny of the cross which produce 50% colored seeds and 50% non-colored seeds are retained. The non-colored seeds will all grow into male-sterile first parent plants of this invention, while the colored seeds will all grow into male-fertile second parent plants of this invention.

8. Maintain first and second parent plants by crossing the first and second parent plants and harvesting of the progeny from the male-sterile first parent plant.

Progeny Table of $A^{S/S,-/-}$ x $A^{S/S,Rf/-}$

|  | S,Rf | S,- |
|---|---|---|
| S,- | $A^{S/S,Rf/-}$ | $A^{S/S,-/-}$ |

Seeds which grow into sterile and fertile plants can be separated on the basis of seed color.

FIGURE 1 (ter)

USE OF ANTHOCYANIN GENES TO MAINTAIN MALE STERILE PLANTS

The present invention relates to a method to maintain male-sterile plants that can be used for the production of hybrid seed of a plant crop species, to transgenic inbred plants that can be used in such process, and to chimeric genes that can be used to produce such transgenic inbred plants.

BACKGROUND OF THE INVENTION

In many, if not most plant species, the development of hybrid cultivars is highly desired because of their generally increased productivity due to heterosis: the superiority of performance of hybrid individuals compared with their parents (see e.g. Fehr, 1987, Principles of cultivar development, Volume 1 : Theory and Technique, MacMillan Publishing Company, New York; Allard, 1960, Principles of Plant Breeding, John Wiley and Sons, Inc.).

The development of hybrid cultivars of various plant species depends upon the capability of achieving essentially almost complete cross-pollination between parents. This is most simply achieved by rendering one of the parent lines male sterile (i.e. bringing them in a condition so that pollen is absent or nonfunctional) either manually, by removing the anthers, or genetically by using, in the one parent, cytoplasmic and/or nuclear genes that prevent anther and/or pollen development (for a review of the genetics of male sterility in plants see Kaul, 1988, 'Male Sterility in Higher Plants', Springer Verlag).

For hybrid plants where the seed is the harvested product (e.g. corn, oilseed rape) it is in most cases also necessary to ensure that fertility of the hybrid plants is fully restored. In systems in which the male sterility is under genetic control this requires the existence and use of genes that can restore male fertility. The development of hybrid cultivars is mainly dependent on the availability of suitable and effective sterility and restorer genes.

Endogenous nuclear loci are known for most plant species that may contain genotypes which effect male sterility, and generally, such loci need to be homozygous for particular recessive alleles in order to result in a male-sterile phenotype. The presence of a dominant 'male fertile' allele at such loci results in male fertility.

Recently it has been shown that male sterility can be induced in a plant by providing the genome of the plant with a chimeric male-sterility gene comprising a DNA sequence (or male-sterility DNA) coding, for example, for a cytotoxic product (such as an RNase) and under the control of a promoter which is predominantly active in selected tissue of the male reproductive organs. In this regard stamen-specific promoters, such as the promoter of the TA29 gene of Nicotiana tabacum, have been shown to be particularly useful for this purpose (Mariani et al., 1990, Nature 347:737, European patent publication ("EP") 0,344,029). By providing the nuclear genome of the plant with such a male-sterility gene, an artificial male-sterility locus is created containing the artificial male- sterility genotype that results in a male-sterile plant.

In addition it has been shown that male fertility can be restored to the plant with a chimeric fertility-restorer gene comprising another DNA sequence (or fertility-restorer DNA) that codes, for example, for a protein that inhibits the activity of the cytotoxic product or otherwise prevents the cytotoxic product from being active in the plant cells (European patent publication "EP" 0,412,911). For example the barnase gene of Bacillus amyloliquefaciens codes for an RNase, called barnase, which can be inhibited by a protein, barstar, that is encoded by the barstar gene of B. amyloliquefaciens. The barnase gene can be used for the construction of a sterility gene while the barstar gene can be used for the construction of a fertility-restorer gene. Experiments in different plant species, e.g. oilseed rape, have shown that a chimeric barstar gene can fully restore the male fertility of male sterile lines in which the male sterility was due to the presence of a chimeric barnase gene (EP 0,412,911, Mariani et al., 1991, Proceedings of the CCIRC Rapeseed Congress, Jul. 9–11, 1991, Saskatoon, Saskatchewan, Canada; Mariani et al., 1992, Nature 357:384). By coupling a marker gene, such as a dominant herbicide resistance gene (for example the bar gene coding for phosphinothricin acetyl transferase (PAT) that converts the herbicidal phosphinothricin to a non-toxic compound [De Block et al., 1987, EMBO J. 6:2513]), to the chimeric male-sterility and/or fertility-restorer gene, breeding systems can be implemented to select for uniform populations of male sterile plants (EP 0,344,029; EP 0,412,911).

The production of hybrid seed of any particular cultivar of a plant species requires the: 1) maintenance of small quantities of pure seed of each inbred parent, and 2) the preparation of larger quantities of seed of each inbred parent. Such larger quantities of seed would normally be obtained by several (usually two) seed multiplication rounds, starting from a small quantity of pure seed ("basic seed") and leading, in each multiplication round, to a larger quantity of pure seed of the inbred parent and then finally to a stock of seed of the inbred parent (the "parent seed" or "foundation seed") which is of sufficient quantity to be planted to produce the desired quantities of hybrid seed. Of course, in each seed multiplication round larger planting areas (fields) are required.

In order to maintain and enlarge a small stock of seeds that can give rise to male-sterile plants it is necessary to cross the male sterile plants with normal pollen-producing parent plants. In the case in which the male-sterility is encoded in the nuclear genome, the offspring of such cross will in all cases be a mixture of male-sterile and male-fertile plants and the latter have to be removed from the former. With male-sterile plants containing an artificial male-sterility locus as described above, such removal can be facilitated by genetically linking the chimeric male sterility gene to a suitable marker gene, such as the bar gene, which allows the easy identification and removal of male-fertile plants (e.g. by spraying of an appropriate herbicide).

However, even when suitable marker genes are linked to male-sterility genotypes, the maintenance of parent male-sterile plants still requires at each generation the removal from the field of a substantial number of plants. For instance in systems using a herbicide resistance gene (e.g. the bar gene) linked to a chimeric male-sterility gene, as outlined above, only half of the parent stock will result in male-sterile plants, thus requiring the removal of the male-fertile plants by herbicide spraying prior to flowering. In any given field, the removal of male-fertile plants effectively reduces the potential yield of hybrid seed or the potential yield of male-sterile plants during each round of seed multiplication for producing parent seed. In addition removal of the male-fertile plants may lead to irregular stands of the male-sterile plants. For these reasons removal of the male-fertile plants is economically unattractive for many important crop species such as corn and oilseed rape.

Anthocyanins are pigments that are responsible for many of the red and blue colors in plants. The genetic basis of anthocyanin biosynthesis has been well characterized, particularly in corn, Petunia, and Antirrhinium (Dooner et al, 1991, Ann.Rev.Genet. 25:179–199; Jayaram and Peterson, 1990, Plant Breeding Reviews 2:91-137; Coe, 1994, In 'The Maize Handbook', Freeling and Walbot, eds. Springer Verlag New York Inc., p. 279–281). In corn anthocyanin biosynthesis is apparently under control of 20 or more genes. The structural loci C2, Whp, A1, A2, Bz1, and Bz2 code for various enzymes involved in anthocyanin biosynthesis and at least 6 regulatory loci, acting upon the structural genes, have been identified in corn i.e. the R, B, Cl, P1, P and Vp1 loci.

The R locus has turned out to be a gene family (in corn located on chromosome 10) comprising at least three different genes i.e. R (which itself may comprise duplicate genes organized in a tandem array), and the displaced duplicate genes R(Sn) and R(Lc). R typically conditions pigmentation of the aleurone but various alleles are known to confer distinct patterns of pigmentation. R(Lc) is associated with unique pigmentation of leaves and R(Sn) with unique pigmentation of the scutellar node. One state of R is associated with pigmentation of the whole plant (R(P)), while another is associated with pigmentation of the seeds (R(S)).

Alleles of the unlinked B locus (in corn located on chromosome 2) rarely condition pigmentation of the aleurone, but are frequently associated with pigmentation of mature plant parts. The B-peru allele however, pigments the aleurone (like R(S)). Analysis at the molecular level has confirmed that the R and B loci are duplicate genes.

In order that the R and B loci can color a particular tissue, the appropriate allele of C1 or P1 loci also needs to be present. The C1 and C1-S alleles, for instance, pigment the aleurone when combined with the suitable R or B allele.

Alleles of the C1 locus have been cloned and sequenced. Of particular interest are C1 (Paz-Ares et al, 1987, EMBO J. 6:3553–3558) and C1-S (Schleffer et al, 1994, Mol.Gen.Genet. 242:40–48). Analysis of the sequences revealed the presence of two introns in the coding region of the gene. The protein encoded by the C1 and C1-S alleles shares homology with myb proto-oncogenes and is known to be a nuclear protein with DNA-binding capacity acting as transcriptional activators.

The cDNA of the B-peru allele has also been analyzed and sequenced (Radicella et al, 1991, Plant Mol. Biol. 17:127–130). Genomic sequences of B-peru were also isolated and characterized based on the homology between R and B (Chandler et al., 1989, the Plant Cell 1:1175–1183; Radicella et al., 1992, Genes & Development 6:2152–2164). The tissue specificity of anthocyanin production of two different B alleles was shown to be due to differences in the promoter and untranslated leader sequences (Radicella et al, 1992, supra).

Various alleles of the R gene family have also been characterized at the molecular level, e.g. Lc (Ludwig et al, 1989, PNAS 86:7092–7096), R-nj, responsible for pigmentation of the crown of the kernel (Dellaporta et al, 1988, In "Chromosome Structure and Function," Impact of New Concepts, 18th Stadeler Genetics Symposium, Gustafson and Appels, eds. (New York, Plenum press, pp. 263–282)), Sn (Consonni ei al, 1992, Nucl. Acids. Res. 20:373), and R(S) (Perrot and Cone, 1989, Nucl. Acids. Res. 17:8003).

The proteins encoded by the B and R genes share homology with myc proto-oncogenes and have characteristics of transcriptional activators.

It has been shown that various structural and regulatory genes introduced in maize tissues by microprojectiles operate in a manner similar to the endogenous loci and can complement genotypes which are deficient in the introduced genes (Klein et al., 1989, PNAS 86:6681–6685; Goff et al., 1990, EMBO J. 9:2517–2522). The Lc gene was also used as a visible marker for plant transformation (Ludwig et al., 1990, Science 247:449–450). Apart from the above other genes involved in anthocyanin biosynthesis have been cloned (Cone, 1994, In 'The Maize Handbook', Freeling and Walbot eds., Springer Verlag New York Inc., p. 282–285).

In Barley, Falk et al (1981, In Barley Genetics IV, proceedings of the 4th International Barley Genetics symposium, Edinburgh University press, Edinburgh, pp. 778–785) have reported the coupling of a male-sterile gene to a xenia-expressing shrunken endosperm gene which makes it possible to select seeds, before planting, that will produce male-sterile plants. Problems asociated with such proposal include complete linkage of the two genes (Stoskopf, 1993, Plant Breeding : Theory and Practice, Westview Press, Boulder, San Francisco, oxford). In sweetcorn, a genetic system to produce hybrid corn seeds without detassling, which utilizes the closely linked genes y (white endosperm) and ms (male sterility) was suggested but was never used because of contamination from 5% recombination. Galinat (1975, J. Hered. 66:387–388) described a two-step seed production scheme that resolved this problem by using electronic color sorters to separate yellow from white kernels . This approach has not been utilized commercially (Kankis and Davis, 1986, in <<Breeding vegetable Crops>>, the Avi Publishing Company Inc. Westport, Conn., U.S.A., p. 498).

EP 0,198,288 and U.S. Pat. No. 4,717,219 describe methods for linking marker genes (which can be visible markers or dominant conditional markers) to endogenous nuclear loci containing nuclear male-sterility genotypes.

EP 412,911 describes foreign restorer genes (e.g. barstar coding region under control of a stamen-specific promoter) that are linked to marker genes, including herbicide resistance genes and genes coding for pigments (e.g. the Al gene) under control of a promoter which directs expression in specific cells, such as petal cells, leaf cells or seed cells, preferably in the outer layer of the seed.

SUMMARY OF THE INVENTION

The invention concerns a maintainer plant consisting essentially of cells which comprise in their genome:
- a homozygous male-sterility genotype at a first genetic locus; and
- a color-linked restorer genotype at a second genetic locus, which is heterozygous (Rf/-)for a foreign DNA Rf comprising:
  a) a fertility-restorer gene capable of preventing the phenotypic expression of said male-sterility genotype, and
  b) at least one anthocyanin regulatory gene involved in the regulation of anthocyanin biosynthesis in cells of seeds of said plant and which is capable of producing anthocyanin at least in the seeds of said plant, so that anthocyanin production in the seeds is visible externally.

The invention also concerns an anthocyanin regulatory gene which is a shortened R, B or C1 gene or a combination of shortened R, B or C1 genes which is functional for conditioning and regulating anthocyanin production in the aleurone.

The invention also includes a DNA such as a plasmid comprising a fertility-restorer gene capable of preventing the phenotypic expression of a male-sterility genotype in a plant and at least one anthocyanin regulatory gene involved in the regulation of anthocyanin biosynthesis in cells of seeds of a plant and which is capable of producing anthocyanin at least in the seeds of a plant, so that anthocyanin production in the seeds is visible externally.

Also within the scope of the invention is a process to maintain a line of male-sterile plants, which comprises the following steps:
i) crossing:
  a) a male-sterile parent plant of said line having, in a first genetic locus, a homozygous male-sterility genotype, and
  b) a maintainer parent plant of said line consisting essentially of cells which comprise, stably integrated in their nuclear genome:
  a homozygous male-sterility genotype at a first genetic locus; and
  a colored-linked restorer genotype at a second genetic locus, which is heterozygous for a foreign DNA comprising:
    i) a fertility-restorer gene capable of preventing the phenotypic expression of said male-sterility genotype, and
    ii) at least one anthocyanin regulatory gene involved in the regulation of anthocyanin biosynthesis in cells of seeds of said plant which is capable of producing anthocyanin at least in the seeds of said plant, so that anthocyanin production in the seeds is visible externally,
ii) obtaining the seeds from said parent plants, and
iii) separating on the basis of color, the seeds in which no anthocyanin is produced and which grow into male-sterile parent plants.

Preferably, the genome of the male-sterile parent plant does not contain at least one anthocyanin regulatory gene necessary for the regulation of anthocyanin biosynthesis in seeds of this plant to produce externally visible anthocyanin in the seeds. In one embodiment of the invention, the genome of the male-sterile parent plant contains a first anthocyanin regulatory gene and the genome of the maintainer plant a second anthocyanin regulatory gene which, when present with the first anthocyanin regulatory gene in the genome of a plant, is capable of conditioning the production of externally visible anthocyanin in seeds.

The invention also concerns a process to maintain a line of maintainer plants, which comprises the following steps:
i) crossing:
  a) a male-sterile parent plant as described previously, and
  b) a maintainer parent plant as described previously,
ii) obtaining the seeds from said male-sterile parent plant, and
iii) separating on the basis of color, the seeds in which anthocyanin is produced and which grow into maintainer parent plants.

The invention also relates to a kit for maintaining a line of male-sterile or maintainer plants, said kit comprising:
a) a male-sterile parent plant of said line as described previously, having, in a first genetic locus, a homozygous male-sterility genotype and which is incapable of producing externally visible anthocyanin in seeds, and
b) a maintainer parent plant of said line as described previously.

Also within the scope of the invention is a process to maintain the kit described previously which comprises:
crossing said male-sterile parent plant with said maintainer parent plant;
obtaining the seeds from said male-sterile parent plants and optionally the seeds from said maintainer parent plant in which no anthocyanin is produced; and
optionally growing said seeds into male-sterile parent plants and maintainer parent plants.

As mentioned above, the present invention provides means to maintain a line of male-sterile plants, particularly corn or wheat plants. These means can be in the form of a process which comprises the following steps:
i) crossing A) a first parent plant of said line, which 5 is male-sterile, and which is genetically characterized by the absence of at least one anthocyanin regulatory gene thereby being incapable of producing anthocyanin in seeds, particularly in the aleurone layer, and also by having at a first genetic locus a homozygous male-sterility genotype, and B) a second parent plant of said line, which is male-fertile, and which is genetically characterized by having at said first genetic locus, said homozygous male- sterility genotype, and at a separate second genetic locus the genotype Rf/−,
whereby,
Rf is a foreign chimeric DNA (the "color-linked restorer gene") stably integrated in the nuclear genome of said plant which comprises:
  a) a fertility-restorer gene that is capable of preventing the phenotypic expression, i.e. the male- sterility, of said male-sterility genotype.
  b) said at least one anthocyanin regulatory gene (the "color gene") involved in the regulation of the anthocyanin biosynthesis in cells of seeds of said cereal plant which is capable of producing anthocyanin at least in the seeds, particularly in the aleurone, of said cereal plant,
ii) obtaining the seeds from said first parent plants
iii) separating, on the basis of color, the seeds in which no anthocyanin is produced and in which the genotype at said first genetic locus is said homozygous male-sterility genotype and the genotype at said second genetic locus is −/−, and the seeds in which anthocyanin is produced and in which the genotype at said first genetic locus is said homozygous male-sterility genotype and the genotype at said second genetic locus is Rf/−.

Of particular interest in the invention is a second parent plant in which said at least one anthocyanin regulatory gene comprises a gene derived from a genomic clone of an R or B gene, particularly an R or B gene that conditions anthocyanin production in the aleurone, preferably the B-peru allele (e.g. the shortened B-peru gene in pCOL13), and/or comprises a gene derived from a genomic clone of the C1 gene (e.g. the gene with the sequence of SEQ ID NO 1 or SEQ ID NO 5) or the C1-S gene.

The first genetic locus can be endogenous to plants of said line (in which case the homozygous male-sterility genotype will be m/m), but is preferably a foreign locus with genotype S/S in which S is a foreign DNA which, when expressed in a plant is capable of rendering the plant male-sterile. A preferred foreign DNA comprises at least:
s1) a male-sterility DNA encoding a RNA, protein or polypeptide which, when produced or overproduced in a cell of the plant, significantly disturbs the metabolism, functioning and/or development of the cell, and,
s2) a sterility promoter capable of directing expression of the male-sterility DNA selectively in stamen cells, preferably tapetum cells, of the plant; the male- sterility DNA being in the same transcriptional unit as, and under the control of, the sterility promoter.

In case such a foreign male-sterility genotype is used, the fertility-restorer gene in the foreign DNA Rf preferably comprises at least:

a1) a fertility-restorer DNA encoding a restorer RNA, protein or polypeptide which, when produced or overproduced in the same stamen cells as said male-sterility gene S, prevents the phenotypic expression of said foreign male-sterility genotype comprising S, and, a2) a restorer promoter capable of directing expression of the fertility-restorer DNA at least in the same stamen cells in which said male-sterility gene S is expressed, so that the phenotypic expression of said male-sterility gene is prevented; the fertility-restorer DNA being in the same transcriptional unit as, and under the control of, the restorer promoter.

In case of an endogenous male-sterility genotype which is homozygous for the recessive male-sterility allele m, the fertility restorer gene is preferably a DNA comprising the dominant allele M of said locus.

The present invention also provides the novel foreign chimeric DNA Rf as used in the second parent plants, plasmids comprising these chimeric genes, and host cells comprising these plasmids.

The present invention also provides the shortened B-peru gene in pCOL13 (SEQ ID NO 6) and the shortened C1 gene, particularly the EcoRI-SfiI fragment of pCOL9 of SEQ ID NO 5.

The present invention further provides plants the nuclear genome of which is transformed with the foreign chimeric DNA Rf, particularly the second parent plant.

DETAILED DESCRIPTION OF THE INVENTION

Figure 2:
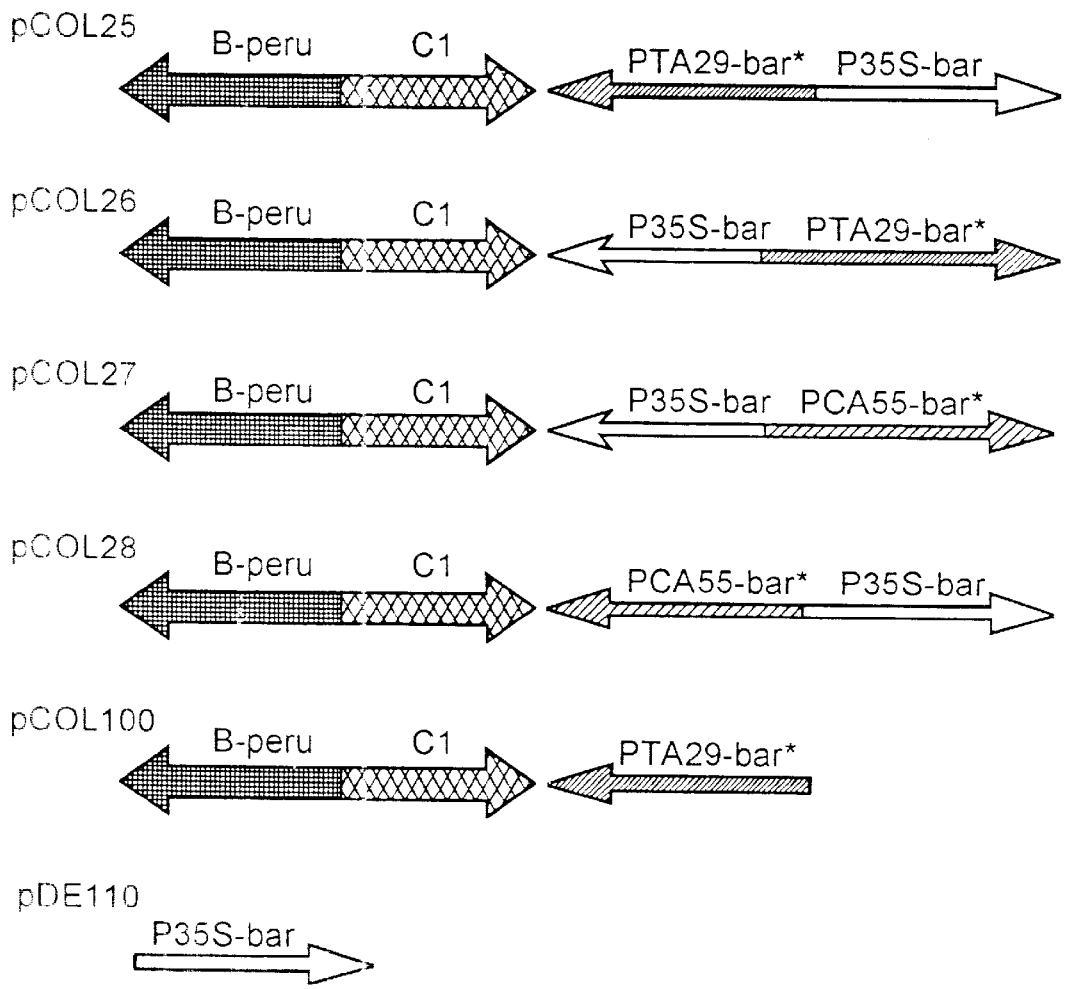

A male-sterile plant is a plant of a given plant species which is male-sterile due to expression of a male-sterility genotype such as a foreign male-sterility genotype containing a male-sterility gene. A restorer plant is a plant of the same plant species that contains within its genome at least one fertility-restorer gene that is able to restore the male fertility in those offspring obtained from a cross between a male-sterile plant and a restorer plant and containing both a male-sterility genotype and a fertility-restorer gene. A restored plant is a plant of the same species that is male-fertile and that contains within its genome a male-sterility genotype and a fertility-restorer gene.

A line is the progeny of a given individual plant.

A gene as used herein is generally understood to comprise at least one coding region coding for an RNA, protein or polypeptide which is operably linked to suitable promoter and 3' regulatory sequences. A structural gene is a gene whose product is a e.g. an enzyme, a structural protein, tRNA or rRNA. For example anthocyanin structural genes encode enzymes (e.g. chalcone synthase) directly involved in the biosynthesis of anthocyanins in plant cells. A regulatory gene is a gene which encodes a regulator protein which regulates the transcription of one or more structural genes. For example the R, B, and C1 genes are regulatory genes that regulate transcription of anthocyanin structural genes.

For the purpose of this invention the expression of a gene, such as a chimeric gene, will mean that the promoter of the gene directs transcription of a DNA into a mRNA which is biologically active i.e. which is either capable of interacting with another RNA, or which is capable of being translated into a biologically active polypeptide or protein.

The phenotype is the external appearance of the expression (or lack of expression) of a genotype i.e. of a gene or set of genes (e.g. male-sterility, seed color, presence of protein or RNA in specific plant tissues etc.)

As used herein, a genetic locus is the position of a given gene in the nuclear genome, i.e. in a particular chromosome, of a plant. Two loci can be on different chromosomes and will segregate independently. Two loci can be located on the same chromosome and are then generally considered as being linked (unless sufficient recombination can occur between them).

An endogenous locus is a locus which is naturally present in a plant. A foreign locus is a locus which is formed in the plant because of the introduction, by means of genetic transformation, of a foreign DNA.

In diploid plants, as in any other diploid organisms, two copies of a gene are present at any autosomal locus. Any gene can be present in the nuclear genome in several variant states designated as alleles. If two identical alleles are present at a locus that locus is designated as being homozygous, if different alleles are present, the locus is designated as being heterozygous. The allelic composition of a locus, or a set of loci, is the genotype. Any allele at a locus is generally represented by a separate symbol (e.g. M and m, S and –, - representing the absence of the gene). A foreign locus is generally characterized by the presence and/or absence of a foreign DNA. A heterozygous genotype in which one allele corresponds to the absence of the foreign DNA is also designated as hemizygous (e.g. Rf/–). A dominant allele is generally represented by a capital letter and is usually associated with the presence of a biologically active gene product (e.g. a protein) and an observable phenotypic effect (e.g. R indicates the production of an active regulator protein and under appropriate conditions anthocyanin production in a given tissue while r indicates that no active regulator protein is produced possibly leading to absence of anthocyanin production).

A plant can be genetically characterized by identification of the allelic state of at least one genetic locus.

The genotype of any given locus can be designated by the symbols for the two alleles that are present at the locus (e.g. M/m or m/m or S/–). The genotype of two unlinked loci can be represented as a sequence of the genotype of each locus (e.g. S/S,Rf/–)

The nuclear male-sterility genotype as used in this invention refers to the genotype of at least one locus, preferably only one locus, in the nuclear genome of a plant (the "male-sterility locus") the allelic composition of which may result in male sterility in the plant. A male-sterility locus may be endogenous to the plant, but it is generally preferred that it is foreign to the plant.

Foreign male-sterility loci are those in which the allele responsible for male sterility is a foreign DNA sequence S (the "male-sterility gene") which when expressed in cells of the plant make the plant male-sterile without otherwise substantially affecting the growth and development of the plant. Such male-sterility gene preferably comprises at least:

s1) a male-sterility DNA encoding a sterility RNA, protein or polypeptide which, when produced or overproduced in a stamen cell of the plant, significantly disturbs the metabolism, functioning and/or development of the stamen cell, and, s2) a sterility promoter capable of directing expression of the male-sterility DNA selectively in stamen cells (e.g. anther cells or tapetum cells) of the plant; the male-sterility DNA being in the same transcriptional unit as, and under the control of, the sterility promoter.

The male-sterility locus preferably also comprises in the same genetic locus at least one first marker gene T which comprises at least:

t1) a first marker DNA encoding a first marker RNA, protein or polypeptide which, when present at least in a specific tissue or specific cells of the plant, renders the plant easily separable from other plants which do not contain the first marker RNA, protein or polypeptide encoded by the first marker DNA at least in the specific tissue or specific cells, and, t2) a first marker promoter capable of directing expression of the first marker DNA at least in the specific tissue or specific cells: the first marker DNA being in the same transcriptional unit as, and under the control of, the first marker promoter.

Such male-sterility gene is always a dominant allele at such a foreign male-sterility locus. The recessive allele corresponds to the absence of the male-sterility gene in the nuclear genome of the plant.

Male-sterility DNAs and sterility promoters that can be used in the male-sterility genes in the first parent line of this invention have been described before (EP 0,344,029 and EP 0,412,911). For the purpose of this invention the expression of the male-sterility gene in a plant cell should be able to be inhibited or repressed for instance by means of expression of a suitable fertility-restorer gene in the same plant cell. In this regard a particular useful male-sterility DNA codes for barnase (Hartley, J. Mol. Biol. 1988 202:913). The sterility promoter can be any promoter but it should at least be active in stamen cells, particularly tapetum cells. Particularly useful sterility promoters are promoters that are selectively active in stamen cells, such as the tapetum-specific promoters of the TA29 gene of *Nicotiana tabacum* (EP 0,344,029) which can be used in tobacco, oilseed rape, lettuce, cichory, corn, rice, wheat and other plant species; the PT72, the PT42 and PE1 promoters from rice which can be used in rice, corn, wheat, and other plant species (WO 92/13956) ; the PCA55 promoter from corn which can be used in corn, rice, wheat and other plant species (WO 92/13957); and the A9 promoter of a tapetum- specific gene of *Arabidopsis thaliana* (Wyatt et al., 1992, Plant Mol. Biol. 19:611–922). However, the sterility promoter may also direct expression of the sterility DNA in cells outside the stamen; particularly if the effect of expression of the male-sterility DNA is such that it will specifically disturb the metabolism, functioning and/or development of stamen cells so that no viable pollen is produced. One example of such a male-sterility DNA is the DNA coding for an antisense RNA which is complementary to the mRNA of the chalcone synthase gene (van der Meer et al (1992) The Plant Cell 4:253–262). In this respect a useful promoter is the 35S promoter (see EP 0,344,029), particularly a 35S promoter that is modified to have enhanced activity in tapetum cells as described by van der Meer et al (1992) The Plant Cell 4:253–262 (the "35S-tap promoter").

A preferred endogenous male-sterility locus is one in which a recessive allele (hereinafter designated as m) in homozygous condition (m/m) results in male sterility. At such loci male fertility is encoded by a corresponding dominant allele (M). In many plant species such endogenous male- sterility loci are known (see Kaul, 1988, supra (in corn see also recent issues of Maize Genetics Cooperation Newsletter, published by Department of Agronomy and U.S. Department of Agriculture, University Of Missouri, Columbia, Mo., U.S.A.). The DNA sequences in the nuclear genome of the plant corresponding to m and M alleles can be identified by gene tagging i.e. by insertional mutagenesis using transposons, or by means of T-DNA integration (see e.g. Wienand and Saedler, 1987, In 'Plant DNA Infectious Agents', Ed. by T. H. Hohn and J. Schell, Springer Verlag Wien New York, p. 205; Shepherd, 1988, In 'Plant Molecular Biology: a Practical Approach', IRL Press, p. 187; Teeri et al., 1986, EMBO J. 5:1755). It will be evident that in the first and second parent plant of this invention S/S can be replaced by m/m without affecting the outcome of the process. Indeed, one feature of the process of this invention is that the male-sterility locus is homozygous thus allowing the use of 'recessive' male-sterility alleles.

Fertility-restorer DNAs that can be used in the fertility restorer gene in the second parent line of this invention have been described before (EP 0,412,911).

In this regard, fertility-restorer genes in which the fertility-restorer DNA encodes barstar (Hartley, J. Mol. Biol. 1988 202:913) are particularly useful to inhibit the expression of a male-sterility DNA that encodes barnase. In this regard it is believed that a fertility-restorer DNA that codes for a mutant of the barstar protein, i.e. one in which the Cysteine residue at position 40 in the protein is replaced by serine (Hartley, 1989, TIBS 14:450), functions better in restoring the fertility in the restored plants of some species.

In principle any promoter can be used as a restorer promoter in the fertility restorer gene in the second parent line of this invention. The only prerequisite is that such second parent plant, which contains both the color gene and the fertility-restorer gene, should be phenotypically normal and male-fertile. This requires that the restorer promoter in the fertility-restorer gene should be at least active in those cells of a plant of the same species in which the sterility promoter of the corresponding male-sterility gene can direct expression of the male-sterility DNA. In this regard it will be preferred that the sterility promoter and the restorer promoter are the same; they can for example be both stamen-specific promoters (e.g. the TA29 promoter or the CA55 promoter) or they can be both constitutive promoters (such as the 35S or 35S-tap promoter). However, the sterility promoter may be active only in stamen cells while the restorer promoter is also active in other cells. For instance, the sterility promoter can be a stamen-specific (such as the TA29 or CA55 promoter) while the restorer promoter is the 35S-tap promoter.

When the male sterility to be restored is due to the male-sterility genotype at an endogenous male-sterility locus being homozygous for a recessive allele m, it is preferred that the fertility-restorer gene is the dominant allele of that male-sterility locus, preferably under control of its own promoter. The DNA corresponding to such a dominant allele, including its natural promoter can be isolated from the nuclear genome of the plant by means of gene tagging as described above.

The nature of the color gene that is used in the color-linked restorer gene in the second parent plant of this invention depends upon the genotype of the untransformed plants of the same line. Preferably, only cereal plants with a genotype that does not condition externally visible anthocyanin production in seeds, particularly in the aleurone can be used to produce the second parent plants. These plants usually have a genotype in which no functional copy of a suitable regulatory gene such as the R or B gene, and/or the C1 gene, is present.

In corn, for instance, all of the currently used inbred lines in the U.S.A. are r-r (pink anthers, leaf tips, plant base) or r-g (green) and most of these are cl and pl; at the B- locus the B-peru allele is very rare (Coe et al, 1988, In 'Corn and Corn Improvement', 3rd edition, G. F. Sprague and J. W. Dudley, eds. America Science of Agronomy, Inc. Publishers, Madison, Wis., U.S.A.). The result is that no anthocyanins are produced in the aleurone of these lines and that the kernels are yellow. This requires that when these lines are transformed with a color-linked restorer gene, the color gene should consist of a functional R or B gene which conditions anthocyanin production in aleurone, and usually also a functional C1 gene capable of conditioning anthocyanin production in aleurone.

A useful R or B gene is the B-peru gene, but of course also other R genes could be used such as the R(S) gene (Perrot and Cone, 1989, Nucl. Acids Res. 17:8003). In this regard a gene derived from genomic clones of the B-peru gene (Chandler et al, 1989, The Plant Cell 1:1175–1183) is believed to be particularly useful. However the length of this genomic DNA (11 kbp) renders its practical manipulation and use for transformation by direct gene transfer, difficult, certainly in combination with other genes such as the restorer gene and the C1 gene.

In one inventive aspect of this invention it was found that the B-peru gene could be considerably shortened while still retaining, under appropriate conditions, its capability of conditioning anthocyanin production in the aleurone of seeds of cereal plants such as corn. A preferred shortened B-peru gene is that of Example 2.2 and which is contained in plasmid pCOL13 (deposited under accession number LMBP 3041).

A useful C1 gene is the genomic clone as described by Paz-Ares et al, 1987, EMBO J. 6:3553–3558. However the length of this genomic DNA (4 kbp) precludes its practical manipulation and use for transformation by direct gene transfer, certainly in combination with other genes such as the restorer gene and the B-peru gene. Nevertheless other variants of the C1 gene can also be used. In this regard Scheffler et al, 1994, Mol.Gen.Genet. 242:40–48 have described the C1-S allele which differs from the C1 allele of Paz-Ares et al, supra by a few nucleotides in the promoter region near the CAAT box and which is dominant to the wild-type allele (C1) and shows enhanced pigmentation. The C1-S gene can be easily used in this invention by appropriate changes in the C1 gene. For example the TGCAG at positions 935 to 939 in SEQ ID NO 1 (respectively at positions 884–888 in SEQ ID NO 5) can be easily changed to TTAGG yielding a C1-S allele (respectively pCOL9S).

In one inventive aspect of this invention it was found that the C1 gene (and the C1-S gene) could be considerably shortened while still retaining, under appropriate conditions, its capability of conditioning anthocyanin production in the aleurone of seeds of cereal plants such as corn. Preferred shortened C1 genes for instance are those of Example 2.1 such as comprised in pCOL9 which has the sequence of SEQ ID NO 5, particularly as comprised between the EcoRI and SfiI sites of pCOL9, and the corresponding shortened C1-S gene in pCOL9S.

The transcribed region of the shortened B-peru and C1 genes still contain some small introns which can also be deleted without affecting the function of the genes. It is also believed that the shortened B-peru and C1 genes can be somewhat further truncated at their 5' and 3' ends, without affecting their expression in aleurone. In particular it is believed that the sequence between positions 1 and 3272 of SEQ ID NO 6 can also be used as a suitable B-peru gene. It is also believed that this gene can still be truncated at its 3' end down to a position between nucleotides 2940 and 3000 of SEQ ID No. 6.

Although the use of genomic sequences of the B-peru gene and the C1 gene, particularly the shortened B-peru and/or the shortened C1 of C1-S genes, is preferred, chimeric R, B, or C1 genes can also be used. For instance a chimeric gene can be used which comprises the coding region (e.g. obtained from the cDNA) of any functional R or B gene (i.e. which conditions anthocyanin production anywhere in the plant) which is operably linked to the promoter region of a R or B gene which conditions anthocyanin production in the aleurone (such as R(S) or B- peru). Since the presence of anthocyanin does not negatively affect growth, development and functioning of plant cells, a constitutive promoter (e.g. the 35S promoter), or a promoter which directs expression at least in the aleurone can also be used in such a chimeric gene. In this regard the promoter of the C1 gene can also be used to direct expression of a DNA comprising the coding region of suitable R or B gene, particularly the B-peru gene.

Similarly the coding region (e.g. obtained from cDNA) of the C1 gene can be operably linked to the promoter of a gene that directs expression at least in the aleurone. In this regard, the promoter of the B-peru gene can also be used to direct expression of a DNA comprising the coding region of a suitable C1 gene such as that of the C1 gene of SEQ ID No. 1 or of the C1-S gene.

In another inventive aspect of the invention it was found that the the promoters comprised in DNAs characterized by the sequences between positions 1 to 1077, particularly between positions 447 and 1077, quite particularly between positions 447 and 1061 of SEQ ID NO 1, between positions 396 and 1026 of SEQ ID No 5, and between positions 1 to 575, particularly between position 1 to 188 of SEQ ID NO 6 are promoters that predominantly, if not selectively, direct expression of any DNA, preferably a heterologous DNA in the aleurone layer of the seeds of plants.

Of course in those lines in which a functional C1 gene is already present in the genome the color gene can consist only of a suitable functional R or B gene (or a chimeric alternative). Alternatively if a line contains already a functional R or B gene which can condition anthocyanin production in the aleurone, but no functional C1 gene, only a functional C1 gene is required as a color gene.

It is believed that the color genes of this invention are especially useful in cereal plants, and that they are of particular use in corn and wheat, and certainly in corn.

For the purposes of this invention it is preferred that, in the second parent plants the "Rf" locus and the male-sterility (e.g. "S") locus are not linked and segregate separately.

In the second parent plant, the fertility restorer gene, the B-peru gene and the C1 gene are preferably closely linked. This can of course be achieved by introducing these genes in the nuclear genome of the plants as a single transforming foreign DNA (the Rf DNA) thus forming a foreign Rf locus. Alternatively, the fertility restorer gene and the color gene can be separately introduced by cotransformation which usually results in single locus insertions in the plant genome.

The color-linked restorer gene Rf as used in the second parent plant preferably also comprises at least c) a second marker gene which comprises at least:

c1) a second marker DNA encoding a second marker RNA, protein or polypeptide which, when present at least in a specific tissue or specific cells of the plant, renders the plant easily separable from other plants which do not contain the second marker RNA, protein or polypeptide encoded by the second marker DNA at least in the specific tissue or specific cells, and, c2) a second marker promoter capable of directing expression of the second marker DNA at least in the specific tissue or specific cells: the second marker DNA being in the same transcriptional unit as, and under the control of, the second marker promoter.

First and second marker DNAs and first and second marker promoters that can be used in the first and second marker genes of this invention are also well known (EP 0,344,029; EP 0,412,911). In this regard it is preferred that the first and second marker DNA are different, although the first and second marker promoter may be the same.

Foreign DNA such as the fertility-restorer gene, the foreign male-sterility gene, the B-peru and the C1 genes, or the first or second marker gene preferably also are provided with suitable 3' transcription regulation sequences and polyadenylation signals, downstream (i.e. 3') from their coding sequence i.e. respectively the fertility-restorer DNA, the male-sterility DNA, the coding region of a color gene (such as a B-peru gene and/or a C1 gene) or the first or second marker DNA. In this regard either foreign or endogenous transcription 3' end formation and polyadenylation signals suitable for obtaining expression of the chimeric gene can be used. For example, the foreign 3' untranslated ends of genes, such as gene 7 (Velten and Schell (1985) Nucl. Acids Res. 13:6998), the octopine synthase gene (De Greve et al., 1982, J.Mol. Appl. Genet. 1:499; Gielen et al (1983) EMBO J. 3:835; Ingelbrecht et al., 1989, The Plant Cell 1:671) and the nopaline synthase gene of the T-DNA region of *Agrobacterium tumefaciens* Ti-plasmid (De Picker et al., 1982, J.Mol. Appl. Genet. 1:561), or the chalcon synthase gene (Sommer and Saedler, 1986, Mol.Gen.Genet. 202:429–434), or the CaMV 19S/35S transcription unit (Mogen et al., 1990, The Plant Cell 2:1261–1272) can be used. However, it is preferred that the color genes in this invention carry their endogenous transcription 3' end formation and polyadenylation signals.

The fertility-restorer gene, the male-sterility gene, the color gene or the first or second marker gene in accordance with the present invention are generally foreign DNAs, preferably foreign chimeric DNA. In this regard "foreign" and "chimeric" with regard to such DNAs have the same meanings as described in EP 0,344,029 and EP 0,412,911.

The cell of a plant, particularly a plant capable of being infected with Agrobacterium such as most dicotyledonous plants (e.g. *Brassica napus*) and some monocotyledonous plants, can be transformed using a vector that is a disarmed Ti-plasmid containing the male-sterility gene, the color linked restorer gene or both and carried by Agrobacterium. This transformation can be carried out using the procedures described, for example, in EP 0,116,718 and EP 0,270,822. Preferred Ti-plasmid vectors contain the foreign DNA between the border sequences, or at least located to the left of the right border sequence, of the T-DNA of the Ti-plasmid. Of course, other types of vectors can be used to transform the plant cell, using procedures such as direct gene transfer (as described, for example, in EP 0,233,247), pollen mediated transformation (as described, for example, in EP 0,270,356, PCT patent publication "Wo" 85/01856, and U.S. Pat. No. 4,684,611), plant RNA virus-mediated transformation (as described, for example, in EP 0,067,553 and U.S. Pat. No. 4,407,956) and liposome-mediated transformation (as described, for example, in U.S. Pat. No. 4,536,475). Cells of monocotyledonous plants such as the major cereals including corn, rice, wheat, barley, and rye, can be transformed (e.g. by electroporation) using wounded or enzyme-degraded intact tissues capable of forming compact embryogenic callus (such as immature embryos in corn), or the embryogenic callus (such as type I callus in corn) obtained thereof, as described in Wo 92/09696. In case the plant to be transformed is corn, other recently developed methods can also be used such as, for example, the method described for certain lines of corn by Fromm et al., 1990, Bio/Technology 8:833; Gordon-Kamm et al., 1990, Bio/Technology 2:603 and Gould et al., 1991, Plant Physiol. 95:426. In case the plant to be transformed is rice, recently developed methods can also be used such as, for example, the method described for certain lines of rice by Shimamoto et al., 1989, Nature 338:274; Datta et al., 1990, Bio/Technology 8:736; and Hayashimoto et al., 1990, Plant Physiol. 93:857.

The transformed cell can be regenerated into a mature plant and the resulting transformed plant can be used in a conventional breeding scheme to produce more transformed plants with the same characteristics or to introduce the male-sterility gene, the color-linked restorer gene (or both), in other varieties of the same related plant species. Seeds obtained from the transformed plants contain the chimeric gene(s) of this invention as a stable genomic insert. Thus the male-sterility gene, or the color-linked restorer gene of this invention when introduced into a particular line of a plant species can always be introduced into any other line by backcrossing.

The first parent plant of this invention contains the male-sterility gene as a stable insert in its nuclear genome (i.e. it is a male-sterile plant). For the purposes of this invention it is preferred that the first parent plant contains the male-sterility gene in homozygous condition so that it transmits the gene to all of its progeny.

The second parent plant of this invention contains the male-sterility gene and the color-linked restorer gene as stable inserts in its nuclear genome (i.e. it is a restored plant). It is preferred that the male-sterility gene be in homozygous condition so that the second parent plant transmits the gene to all of its progeny and that the color-linked restorer gene be in heterozygous condition so that the second parent plant transmits the gene to only half of its progeny.

It is preferred that the first and second parent plants are produced from the same untransformed line of a plant species, particularly from the same inbred line of that species.

The first and second parent plants of this invention have the particular advantage that seeds of such plants can be maintained indefinitely, and can be amplified to any desired amount (e.g. by continuous crossing of the two plant lines).

The color genes of this invention can be used as marker gene in any situation in which it is worthwhile to detect the presence of a foreign DNA (i.e. a transgene) in seeds of a transformed plant in order to isolate seeds which possess the foreign DNA. In this regard virtually any foreign DNA, particularly a chimeric gene can be linked to the color gene.

Examples of such foreign DNAs are genes coding for insecticidal (e.g. from *Bacillus thuringiensis*), fungicidal or nematocidal proteins. Similarly the color-gene can be linked to a foreign DNA which is the male-sterility gene as used in this invention.

However, the color genes are believed to be of particular use in the process of this invention in which they are present in a foreign DNA which comprises a fertility restorer gene (such as the barstar gene of *Bacillus amyloliguefaciens*) under control of a stamen-specific promoter (such as PTA29). In appropriate conditions the use of the color genes allows the easy separation of harvested seeds that will grow into male-sterile plants, and harvested seeds that will grow into male-fertile plants. In this regard the seeds are preferably harvested from male-sterile plants (the first parent plants) that are homozygous at a male-sterility locus (such as a locus comprising the barnase gene under control of PTA29) and which have been pollinated by restorer plants (the second parent plants of this invention) which contain in their genome two unlinked gene loci one of which comprises the same male-sterility locus which is homozygous for the same male-sterility gene while the other is a foreign locus which comprises an appropriate fertility restorer gene (i.e. whose expression will counteract the expression of the male-sterility gene) and also the color gene of this invention, particularly an R or B gene that is expressed in the aleurone and/or a C1 gene, preferably the B-peru and C1 gene (e.g. as described in the examples). First and second parent plants can be essentially produced as described in the examples and as summarized in FIG. 1. In step 8 of FIG. 1 it is demonstrated that the crossing of the first and second parent plants of this invention will give rise in the progeny to about 50% new first parent (i.e. male- sterile) plants and about 50% new second parent (i.e. male- fertile) plants and that these two types of plants can already be separated at the seed stage on the basis of color. Red kernels will grow into male-fertile plants while yellow kernels will grow into male-sterile plants.

Thus a line of male-sterile first parent plants of this invention can be easily maintained by continued crossing with the second parent plants of this invention with, in each generation, harvesting the seeds from the male-sterile plants and separation of the yellow and red kernels. Of course in this way any desired amount of seed for foundation seed production of a particular line, such as an inbred line, can also be easily obtained.

The red and yellow seeds harvested from a cereal plant (e.g. the first parent plant of this invention) can be separated manually. However, such separation can also be effected mechanically. A color sorting machine for corn kernel and other granular products is for instance available from Xeltron U.S. (Redmond, Was., U.S.A.)

Unless otherwise indicated all experimental procedures for manipulating recombinant DNA were carried out by the standardized procedures described in Sambrook et al., 1989, "Molecular Cloning: a Laboratory Manual", Cold Spring Harbor Laboratory, and Ausubel et al, 1994, "Current Protocols in Molecular Biology", John Wiley & Sons.

The polymerase chain reactions ("PCR") were used to clone and/or amplify DNA fragments. PCR with overlap extension was used in order to construct chimeric genes (Horton et al, 1989, Gene 77:61–68; Ho et al, 1989, Gene 77:51–59).

All PCR reactions were performed under conventional conditions using the Vent$^T$M polymerase (Cat. No. 254L - Biolabs New England, Beverley, Mass. 01915, U.S.A.) isolated from *Thermococcus litoralis* (Neuner et al., 1990, Arch.Microbiol. 15:205–207). Oligonucleotides were designed according to known rules as outlined for example by Kramer and Fritz (1968, Methods in Enzymology 154:350), and synthesized by the phosphoramidite method (Beaucage and Caruthers, 1981, Tetrahedron Letters 22:1859) on an applied Biosystems 380A DNA synthesizer (Applied Biosystems B. V., Maarssen, Netherlands).

In the following examples, reference will be made to the following sequence listing and figures:
Sequence Listing
SEQ ID No 1 : sequence of C1 gene
SEQ ID NO 2 : plasmid pTS256
SEQ ID NO 3 : EcoRI-HindIII region of pTS200 comprising the chimeric gene PCA55-barstar-3'nos (the omitted region of pTS200 is derived from pUC19.
SEQ ID NO 4 oligonucleotide 1
SEQ ID NO 5 : pCOL9 containing the shortened C1 gene as a EcoRI-SfiI fragment SEQ ID NO 6 : presumed sequence of the EcoRI-HindIII region of pCOL13 containing the shortened B-peru gene (the rest of the plasmid is pUC19). The stretch of N nucleotides corresponds to a region of approximate length which is derived from the genomic clone of the B-peru gene but for which the sequence needs to be confirmed.
SEQ ID NO 7 : actual sequence of the EcoRI-HindIII region of pCOL13 containing the shortened B-peru gene (the rest of the plasmid is pUC19).

FIGURES

FIG. 1 : Breeding scheme to obtain the first and second parent plants of this invention FIG. 2 : Schematic structure of pCOL25, pCOL26, pCOL27, pCOL28, pCOL100 and pDE110.

EXAMPLES

Example 1

Construction of plasmids containing the male-sterility gene comprising the TA29 promoter and the barnase coding region Plasmids useful for transformation of corn plants and carrying a male-sterility gene and a selectable marker gene have been described in WO 92/09696 and WO 92/00275.

Plasmid pVE107 contains the following chimeric genes:
1) PTA29-barnase-3'nos, i.e. a DNA coding for barnase of *Bacillus amyloliguefaciens* (barnase) operably linked to the stamen-specific promoter of the TA29 gene of *Nicotiana tabacum* (PTA29) and the 3' regulatory sequence containing the polyadenylation signal of the nopaline synthase gene of *Agrobacterium tumefaciens* (3'nos), and 2) P35S-neo-3'ocs, i.e. the coding region of the gene of Tn5 of *E.coli* coding for neomycin phosphotransferase (neo) operably linked to the 35S promoter of Cauliflower Mosaic Virus (P35S) and the 3' regulatory sequence containing the polyadenylation signal of the octopine synthase gene of *Agrobacterium tumefaciens* (3'ocs).

Plasmid pVE108 contains the following chimeric genes: 1) PTA29-barnase-3'nos, and 2) P35S-bar-3'nos, i.e. the gene of *Streptomyces hygroscopicus* (EP 242236) coding for phosphinothricin acetyl transferase (bar) operably linked to the P35S and 3'nos.

PTA29-barnase-3'nos is an example of a foreign chimeric male-sterility gene (S) used in this invention.

Example 2

Construction of a plasmid containing the color-linked restorer gene 2.1. Obtaining a shortened functional C1 gene The C1 gene of maize was cloned from transposable-induced mutants and its sequence was reported (Paz-Ares, 1987, EMBO J. 6:3553–3558). This sequence is reproduced in SEQ ID NO. 1. Plasmid p36 (alternatively designated as pC1LC5kb and further designated as plasmid pXXO36) comprising a C1 genomic clone was obtained from Dr. H. Saedler and Dr. U. Wienand of the Max- Planck Institut für Züchtungsforschung, Köln, Germany. pXX036 was digested with SnabI and HindIII, filled-in with Klenow, and selfligated, yielding plasmid pCOL9. pCOL9 corresponds to pUC19 (Yanisch-Perron et al, 1985, Gene 5 33:103–119) which contains, between its EcoRI and modified HindIII sites, the 2189 bp EcoRI-SnabI fragment (corresponding to the sequence between positions 448 and 2637 of SEQ ID NO 1) of pXX036.

pXXO36 was also digested with SfiI and HindIII and treated with Klenow to make blunt ends. After ligation the plasmid in which the DNA downstream from the SfiI site was deleted was designated as pCOL12.

The sequence TGCAG in pCOL9, corresponding to the sequence at positions 884 to 888 in SEQ ID NO 5, is changed to TTAGG, yielding pCOL9S which instead of a shortened C1 gene contains a shortened overexpressing C1-S gene (Schleffer et al, 1994, Mol.Gen.Genet. 242:40–48). A similar change is introduced in pCOL12, yielding pCOL12S.

2.2. Obtaining a shortened functional B-peru gene

Plasmid pBP2 (further designated as pXX004) is plasmid pTZ18U (Mead et al., 1986, Protein Engineering 1:67; U.S.Biochemical Corp.) containing the genomic clone of the B- peru gene. Plasmid p35SBPcDNA (further designated as pXX002) is plasmid pMF6 (Goff et al, 1990, EMBO J. 9:2517–2522) containing the cDNA corresponding to the B-peru gene. Both plasmids were obtained from Dr. V. Chandler of the University of Oregon, Oregon, U.S.A. A 2660 bp sequence of the genomic clone around the translation initiation codon was reported (EMBL/Genbank/DDBJ databases; locus name ZMBPERUA, Accession number X70791; see also Radicella et al, 1992, Genes & Development 6:2152–2164). The sequence of the B-peru CDNA was also reported (Radicella et al, 1991, Plant Mol. Biol. 17:127–130).

Substantial amounts of 5' and 3' flanking sequences were deleted from pXXOO4, and the MluI-MunI fragment in the coding region of the genomic clone was replaced by the 1615 bp MluI- MunI fragment of the cDNA clone. The resulting plasmid was designated as pCOL13 which was deposited at the Belgian Coordinated Collection of Microorganisms—LMBP Collection, Laboratory Molecular Biology, University of Ghent, K. L. Ledeganckstraat 35, B-9000 Ghent, Belgium and was given the Accession Number LMBP 3041. A shortened but functional B-peru gene is contained in pCOL13 as an EcoRI-SalI fragment with an approximate length of 4 kbp (see SEQ ID NO 6).

2.3. Combining the C1 and B-peru genes

The C1 gene in pCOL9 and the B-peru gene in pCOL13 were then combined as follows. The 4 kbp EcoRI-SalI fragment of pCOL13 was introduced between the EcoRI and SalI sites of the vector pBluescript II SK(−) (Stratagene), yielding #7 B SK(−). pCOL9 was digested with SfiI, treated with Klenow to fill in protruding ends, and further digested with EcoRI. The 1978 bp SfiI(Klenow)/EcoRI was then introduced between the EcoRI and SmaI sites of #7 B SK(−), yielding #7 B+C SK(−). Finally the XhoI site in the C1 sequence was removed as follows. The 950 bp EcoRI-SacII fragment of #7 B SK(−) (EcoRI site corresponding to the EcoRI site at position 1506 in SEQ ID NO 1; the SacII site from the pBluescript linker) was introduced between the EcoRI and SacII sites of the Phagescript Vector (Stratagene) to yield pCOL21. Single strands of pCOL21 were prepared and hybridized to the following synthetic oligonucleotide 1 (SEQ ID No. 4):

5'-CGT TTC TCG AAT CCG ACG AGG-3' resulting in a silent change (CTCGAG→CTCGAA) and removal of the XhoI site.

The 710 AatII-SacII fragment of #7 B SK(−) was then exchanged for the corresponding AatII-SacII fragment of the mutated pCOL21, yielding pCOL23.

pCOL23 was then linearized with SacII, treated with Klenow, and ligated to XhoI linker sequence (Stratagene), yielding pCOL24.

Using the same procedure as described above, the shortened C1-S gene of pCOL9S is combined with the shortened B-peru gene of pCOL23, yielding plasmid pCOL24S.

2.4. Construction of vectors comprising the C1 and B-peru genes as well as male-sterility gene and a selectable marker gene pTS256 is derived from pUC19 and contains the following two chimeric genes :1) P35S-bar-3'nos, and 2) PTA29-barstar- 3'nos, i.e. a DNA coding for barstar of *Bacillus amyloliguefaciens* (barstar or bar*) operably linked to PTA29 and 3'nos. The complete sequence of pTS256 is given in SEQ ID NO 2.

pTS200 is derived from pUC19 and contains the following two chimeric genes 1) P35S-bar-3'nos, and 2) PCA55-barstar- 3'nos, i.e. barstar operably linked to the stamen-specific promoter PCA55 of *Zea mays* and 3'nos. The complete sequence of pTS200 is given in SEQ ID NO 3.

pTS256 was modified by the inclusion of NotI linkers (Stratagene) in both the unique SspI and SmaI sites, yielding pTS256NN. The shorter BspEI-SacII fragment of pTS256NN was then replaced by the shorter BspEI-SacII fragment of pTS200, yielding pTS256+200.

pTS256NN contains P35S-bar3'-nos and pTA29-barstar3'nos on a NotI cassette. pTS256NN+200 contains P35S-bar3'-nos and pCA55- barstar3'nos on a NotI cassette.

The NotI cassette of pTS256NN was introduced in the NotI site of pCOL24, yielding pCOL25 and pCOL26 which differ with respect to the orientation of the P35S-bar3'-nos gene with respect to the shortened C1 gene (FIG. 2).

The NotI cassette of pTS256NN+200 was introduced in the NotI site of pCOL24, yielding pCOL27 and pCOL28 which differ with respect to the orientation of the P35S-bar3'-nos gene with respect to the shortened C1 gene (FIG. 2).

Plasmids pCOL25, pCOL26, pCOL27 or pCOL28 contain a color- linked restorer gene Rf and a selectable marker gene (P35S-bar- 3'nos). Rf comprises the shortened C1 and B-peru genes and a chimeric barstar gene (either PTA29-barstar-3'nos or PCA55- barstar-3'nos).

Plasmids pCOL25S, pCOL26S, pCOL27S or pCOL28S, containing the shortened C1-S gene instead of the shortened C1 gene, are obtained in a similar way using pCOL24S instead of pCOL24.

2.5. Construction of vectors comprising the C1 and B-peru genes as well as male-sterility gene Plasmid pTS59 can be obtained from plasmid pTS256 (of SEQ ID NO 2) by replacing the fragment extending from positions 1 to 1470 (comprising the chimeric gene P35S-bar-3'nos) with the sequence TATGATA. Then NotI linkers (Stratagene) were introduced in the EcoRV and SmaI sites of pTS59; yielding pTS59NN. Finally the NotI fragment comprising the chimeric gene PTA29-barstar-3'nos was; introduced in the NotI site of #7 B+C SK(−), yielding pCOL100 (the general structure of pCOL100 and pDE110 is also presented in FIG. 2).

2.6. Expression of shortened C1 and B-peru in aleurone in corn seeds

Dry seeds were incubated overnight in water at room temperature and were then peeled and sliced in half. Four to six half kernels were placed with the cut side on wet filter paper and were bombarded with tungsten particles (diameter 0.7 μm) which were coated with DNA.

Particle bombardment was essentially carried out using the particle gun and procedures as described by Zumbrunn et al, 1989, Technique, 1:204–216. The tissue was placed at 10 cm from the stopping plate while a 100 μm mesh was placed at 5 cm from the stopping plate.

DNA of the following plasmids was used:

pXXOO2 : B-peru cDNA under control of the 35S promoter pXX201 : Cl CDNA under control of the 35S promoter pCOL13 : shortened B-peru gene as described in Example 2.2 pCOL12 : shortened C1 gene as described in Example 2.1 pCOL100 : shortened B-peru and shortened Cl and PTA29-barstar-3'nos as described in Example 2.5.

After bombardment the tissue was incubated for 2 days on wet filter paper at 27° C. and was then checked for the presence of red spots indicating anthocyanin production.

TABLE 1

|  |  |  | pXX00 | PXX201 | pXX002 pXX201 | pCOL13 | pCOL12 | pCOL100 |
|---|---|---|---|---|---|---|---|---|
| H99 | r | cl | – | – | + | nt | nt | nt |
| Pa91 | r | cl | – | – | + | nt | nt | nt |
| B73 | r | cl | – | – | + | nt | nt | + |
| inbred1 | r | cl | – | – | + | nt | nt | nt |
| inbred2 | r | cl | – | – | + | nt | nt | nt |
| inbred3 | r | cl | – | – | + | nt | nt | nt |
| inbred4 | r | cl | + | – | + | + | – | nt |
| inbred5 | r | cl | + | – | + | + | – | nt |
| inbred6 | r | cl | – | – | + | nt | nt | nt |
| inbred7 | r | cl | – | – | + | nt | nt | nt |
| inbred8 | r | cl | – | – | + | nt | nt | nt |
| inbred9 | r | cl | + | – | + | + | – | nt |
| c-ruq | R | cl | – | + | + | – | + | nt |

Note: + indicates that anthocyanin production was observed in at least one experiment; – indicates that no anthocyanin production was observed, nt = not tested.

The results for three public lines (H99, Pa91, B73) and 9 different, commercially important, proprietary inbred lines from various sources are shown in Table 1. The line c-ruq is a tester line which is homozygous for a C1 allele that is inactivated by insertion of a receptor for the regulator Uq (Cormack et al., 1988, Crop Sci. 28:941–944).

All lines which were r and cl produced anthocyanin in the aleurone after introduction with both a functional B-peru and C1 gene. Lines which were R and cl produced anthocyanin upon introduction of a functional C1 gene. Lines which were r and C1 produced anthocyanin upon introduction of a functional B-peru gene. This proves that the B-peru and C1 gene is sufficient for anthocyanin production in most corn lines. From the data in Table 1 it is also evident that even the shortened B-peru and C1 genes are still functional and are capable of producing anthocyanin in aleurone of corn lines with suitable genotypes.

Example 3

Production of first parent corn plants by transformation of corn with the plasmids of example 1

Corn plants of line H99, transformed with a male-sterility gene comprising a DNA encoding barnase of *Bacillus amyloliguefaciens* under control of the promoter of the TA29 gene of *Nicotiana tabacum* have been described in Wo 92/09696. The transformed plants were shown to be male-sterile.

Example 4

Production of second parent corn plants by transformation of corn with the plasmids of examples 2

Corn inbred lines H99 and Pa91 are transformed using the procedures as described in Wo 92/09696 but using plasmids pCOL25, pCOL26, pCOL27 or pCOL28 of Example 2. Regenerated plants are selected that are male fertile and in which the shortened C1, the shortened B-peru gene, the P35S-bar-3'nos gene, and the PTA29- barstar-3'nos (or PCA55-barstar-3'nos) are expressed.

Alternatively the male-sterile plants of Example 3 (already containing the S gene) can be transformed with plasmids pCOL25, pCOL26, pCOL27 or pCOL28 of Example 2 on the condition that the S and Rf genes are linked to different selectable marker genes.

Similarly, transformed corn plants are obtained using plasmids pCOL25S, pCOL26S, pCOL27S or pCOL28S of Example 2.

In an alternative set of experiments the second parent plants of this invention were obtained by transforming corn plants of line H99, Pa91, and (Pa91×H99)x H99 with two separate plasmids one of which contained the color linked restorer gene (pCOL100), while the other contains an appropriate selectable marker gene such as a chimeric bar gene (pDE110) (alternatively a chimeric neo gene may also be used). pDE110 was described in Wo 92/09696 and the construction of pCOL100 was described in Example 2.5.

In yet another set of experiments the second parent plants of this invention are obtained by transforming corn plants with a purified fragment of the plasmids of example 2.4. Such purified fragment is obtained by digestion of the plasmids of example 2.4 with XhoI and subsequent purification using conventional procedures such as gel filtration.

Untransformed corn plants of lines E99 or Pa91 are detasseled and pollinated with pollen of the plants transformed with the Rf DNA. It is observed that the f gene segregates in a Mendelian way and that the seed that is harvested from these plants is colored and non-colored (yellow) in a 1:1 ratio. The red color of the seeds is correlated with the presence of the Rf gene.

Example 5

The production of the first and second parent plants of this invention

First parent plants and second parent plants (i.e. maintainer plants) according to the invention are produced along the lines set out in FIG. 1.

The male-sterile plants of step 1 are those produced in Example 1. The corn plants transformed with the color-linked restorer gene of step 2 are those produced in Example 4.

A plant of Example 1 and a plant of Example 4 are crossed (Step 3) and the progeny plants with the genotype S/-, Rf/- are selected (Step 4), e.g. by demonstrating the presence of both the S and Rf genes in the nuclear genome (e.g. by means of PCR).

The plants selected in Step 4 are then crossed with the male-sterile plants with genotype S/- (Step 5). The colored seeds (i.e. those containing the Rf gene) are selected, grown into plants, and examined for the presence of both the S and Rf genes (e.g. by PCR). The plants containing both the S and Rf genes are selfed and the seeds of each plant are examined on seed color (red or yellow). From the progeny of the selfings the non-colored seeds are grown into plants (step 6). The progeny of the selfings in which all noncolored seeds grow into male-sterile plants are retained (Step 6). These male-sterile plants are all homozygous for the S gene and are crossed with their fertile siblings (of genotype S/S,Rf/Rf or S/S,Rf/-) (Step 7). For some crossings the seeds harvested from the male-sterile plants are 50% colored and 50% non-colored (step 7). The colored seeds all grow into fertile corn plants of genotype S/S,Rf/– which are the maintainer plants, or the second parent plants, of the present invention. The noncolored seeds all grow into male-sterile plants of the genotype S/S,–/– which are the first parent plants of this invention (Step 7).

The first and second parent plants are crossed and the seeds harvested from the male-sterile plants are separated on the basis of color (Step 8). All colored seeds grow again in second parent plants and all noncolored seeds grow in first parent plants, thereby establishing an easy maintenance of a pure male-sterile line of corn.

If the plant DNA that is flanking the S gene in the plants of Example 1 has been characterized, the progeny of the cross in Step 5 with genotypes S/S,-I- and S/S,R/- can be easily identified by means of PCR using probes corresponding to the flanking plant DNA. In this way Step 6 can be skipped because the plants of Step 5 which grow from colored seeds (genotype S/S,Rf/-) can be crossed directly to plants with genotype S/S,-I- (as in Step 7).

All publications cited in this application are hereby incorporated by reference.

Example 6

Maintainer plants containing a color-linked restorer gene comprising the B-Peru coding region under control of the Promoter of the C1-S gene Using conventional techniques a chimeric gene is inserted between the EcoRI and HindIII sites of the polylinker of plasmid pUC19. The chimeric gene comprises the following elements in sequence:

i) the promoter region of the C1-S gene, i.e. the DNA fragment with the sequence of SEQ ID No. 1 from nucleotide positions 447 up to 1076 but containing at nucleotide positions 935–939 the sequence TTAGG instead of TGCAG.

ii) a single C nucleotide iii) the coding region and 3'untranslated region of the B-peru gene, i.e. the DNA fragment with the sequence of SEQ ID No. 7 from nucleotide positions 576 up to 4137.

This plasmid (designated as pLH52), together with plasmid pCOL9S of Example 2 (comprising a C1-S gene) and pTS256 of SEQ ID No. 2 (comprising the following chimeric genes: P35S-bar-3'nos and PTA29-barstar-3'nos), is used to transform corn essentially as described in Example 4. The transformed plants are then used to obtain second parent plants as described in Example 5.

Example 7

Maintainer plants containing a color-linked restorer gene comprising the B-Peru coding region under control of the 35S promoter Using conventional techniques a chimeric gene is inserted between the EcoRI and HindIII sites of the polylinker of plasmid pUC19. the chimeric gene comprises the following elements in sequence:

i) The promoter region of the 35S promoter, i.e. the DNA fragment of pDE110 which essentially has the sequence as described in SEQ ID No. 4 of WO 92/09696 (which is incorporated herein by reference) from nucleotide positions 396 up to 1779 ii) the coding region and 3'untranslated region of the B-peru gene, i.e. the DNA fragment with the sequence of SEQ ID No. 7 from nucleotide positions 576 up to 4137.

This plasmid (designated as pP35S-Bp), together with plasmid pCOL9S of Example 2 (comprising a C1-S gene) and pTS256 of SEQ ID No. 2 (comprising the following chimeric genes: P35S-bar-3'nos and PTA-29-barstar-3'nos), is used to transform corn essentially as described in Example 4. The transformed plants are then used to obtain second parent plants as described in Example 5.

Alternatively plasmid p35SBperu as described in Goff et al, 1990, EMBO 9:2517–2522 is used instead of pP35SBp.

Example 8

Maintainer plants containing a color-linked restorer gene comprising the maize P gene coding region under the control of the promoter of the C1-S gene Using conventional techniques a chimeric gene is inserted in the EcoRI site of the polylinker of plasmid pUC19. The chimeric gene comprises the following elements in sequence:

i) the promoter region of the C1-S gene, i.e. the DNA fragment with the sequence of SEQ ID No. 1 for nucleotide positions 447 up to 1076 but containing at nucleotide positions 935–939 the sequence TTAGG instead of TGCAG ii) a single C nucleotide;

iii) a DNA sequence comprising the coding region and 3'end untranslated region of the maize P gene as described by Grotewold et al in 1991, PNAS 88:4587–4591 (nucleotides 320-1517). The maize P gene is an anthocyanin regulatory gene which specifies red phlobaphene pigmentation, a flavonoid pigment involved in the biosynthetic pathway of anthocyanin. In fact, the protein encoded by the P gene activates, among others, the A1 gene required for both anthocyanin and phlobaphene pigmentation. Two cDNA clones have been isolated and sequenced by Grotewold et al and are described in the publication referred to above. It is the longer cDNA which is of particular interest for construction of this chimeric gene. However, alternatively, the coding region of the shorter transcript can also be used in this chimeric gene, as well as the P gene leader sequence instead of the CI-S gene leader sequence. The P gene does not require a functional R or B gene to produce pigmentation. The visible pigment that is produced in the seeds of the maintainer plants is phlobaphene, a flavonoid pigment (like anthocyanin) directly involved in anthocyanin biosynthesis.

iv) a DNA fragment containing the polyadenylation signal of the nopaline synthase gene of *Agrobacterium tumefaciens*, i.e. the DNA fragment with the sequence of SEQ ID. No. 2 from nucleotide position 1600 up to nucleotide position 2909.

The resulting plasmid (designated as pPCS1-P), together with pTS256 of SEQ ID No. 2 is used to transform corn essentially as described in example 4. The transformed plants are then used to obtain second parent plants as described in example 5.

Example 9

Maintainer plants containing a color-linked restorer gene comprising the B-peru coding region under the control of the B-peru promoter Using conventional techniques a chimeric gene is inserted between the EcoRI and the HindIII sites of the polylinker of plasmid pUC19. The chimeric gene comprises the following elements in sequence:

i) the promoter of the B-peru gene, i.e. a 1952 bp DNA sequence as disclosed in the EMBL databank under accession number X70791;

ii) the coding region and 3'untranslated region of the B-peru gene, i.e. the DNA fragment with the sequence of SEQ ID No. 7 from nucleotide position 576 up to 4137. This plasmid (designated aspCOL11), together with plasmid pCOL 9S of example 2 (comprising a C1-S gene) and pTS256 of SEQ ID No. 2 (comprising the following chimeric genes: P35S-bar-3'nos and PTA29-barstar-3'nos) is used to transform corn essentially as described in example 4. The transformed plants are then used to obtain second parent plants as described in example 5.

---

We claim:

1. A process for maintaining a line of male-sterile plants or of maintainer plants, said process comprising:
   (i) crossing:
      (a) a male-sterile line comprising male-sterile parent plants which comprise a homozygous male-sterility genotype at a first genetic locus and which lack at least one functional regulatory gene required for anthocyanin production in the seeds, and
      (b) a maintainer line comprising male-fertile parent plants which comprise said homozygous male-sterility genotype at said first genetic locus, and which further comprise at a second genetic locus which segregates independently from said first genetic locus, a foreign DNA comprising:
         i) a restorer gene, the expression of which prevents the phenotypic expression of said homozygous male-sterility genotype, and
         ii) at least one anthocyanin regulatory gene involved in the regulation of anthocyanin biosynthesis in the cells of seeds of said plant which is capable of producing anthocyanin at least in the seeds of said plant so that anthocyanin production in the seeds is visible externally;
      wherein said foreign DNA is heterozygous at said second genetic locus, and wherein said male-sterile plants produce seeds producing anthocyanin, as well as seeds not producing anthocyanin, said anthocyanin being produced only in seeds comprising said at least one anthocyanin regulatory gene in said foreign DNA;
   (ii) harvesting seeds from said male-sterile parent plants; and
   (iii) selecting from the harvested seeds, either those seeds which do not produce anthocyanin, said selected seeds being capable of growing into a new generation of male-sterile plants, or selecting those seeds which produce anthocyanin, said selected seeds being capable of growing into a new generation of male-fertile plants.

2. The process of claim 1, in which said at least one anthocyanin regulatory gene is capable of producing anthocyanin at least in the aleurone of seeds.

3. The process of claim 1, in which said first genetic locus is a foreign genetic locus and comprises a male-sterility gene which, if present in a plant in the absence of said restorer genotype, would render the plant male-sterile, and wherein said male-sterility gene is homozygous at said first genetic locus.

4. The process of claim 3, wherein said male-sterility genotype at said first genetic locus comprises a foreign DNA which comprises a male-sterility gene comprising:
   a male-sterility DNA encoding an RNA, protein or polypeptide which, when produced or overproduced in a stamen cell, significantly disturbs the metabolism, functioning and/or development of said cell; and
   a sterility promoter capable of directing expression of said male-sterility DNA selectively in the stamen cells of the plant; the male-sterility DNA being in the same transcriptional unit as, and under the control of, the sterility promoter;
and in which said restorer genotype at said second genetic locus comprises a foreign DNA which comprises a restorer gene which comprises:
   a fertility-restorer DNA encoding a restorer RNA, protein or polypeptide which, when expressed in the same cell as said male-sterility gene, prevents the phenotypic expression of said male-sterility gene; and
   a restorer promoter capable of directing expression of said fertility-restorer DNA at least in the same cells in which said male-sterility gene is expressed, so that the phenotypic expression of said male-sterility gene is prevented; said fertility-restorer DNA being in the same transcriptional unit as, and under the control of, said restorer promoter.

5. The process of claim 4, wherein said male-sterility DNA encodes a barnase and said fertility-restorer DNA encodes a barstar.

6. The process of claim 4, wherein said sterility promoter is a TA29 promoter or a CA55 promoter.

7. The process of claim 4, in which said sterility promoter is a PT72, PT42 or PE1 promoter.

8. The process of claim 4, in which said restorer promoter is identical to said sterility promoter.

9. The process of claim 8, in which said restorer promoter is a TA29 promoter or a CA55 promoter.

10. The process of claim 1, in which said first genetic locus is an endogenous male-sterility locus, comprising a recessive allele in homozygous condition, and in which said restorer gene is the dominant allele at said endogenous male-sterility locus.

11. The process of claim 1, in which said male-sterile parent plants contain a first anthocyanin regulatory gene involved in the regulation of anthocyanin biosynthesis in the cells of seeds that is functionally expressed in the seeds and said male-fertile parent plants contain a second anthocyanin regulatory gene which, when present with said first anthocyanin regulatory gene in the genome of a plant, is capable of conditioning the production of anthocyanin in the seeds which is visible externally.

12. The process of claim 1, wherein said at least one anthocyanin regulatory gene is selected from the group of a first gene that is expressed in seeds to produce a first active regulatory protein having the same activity as the protein encoded by a functional R or B gene, and a second gene that is expressed in seeds to produce a second active regulatory protein having the same activity as the protein encoded by a functional C1 gene.

13. The process of claim 12, wherein said male-fertile parent plants comprise said first gene involved in the regulation of anthocyanin biosynthesis in the cells of seeds that is functionally expressed in the seeds in said foreign DNA, and wherein said male-sterile parent plants do not contain a gene that is functionally expressed in the seeds which encodes an active regulatory protein having the same activity as the protein encoded by a functional R or B gene.

14. The process of claim 13, in which said first gene comprises a DNA encoding a B-peru protein which is under the control of a promoter of the B-peru gene, a promoter comprising the nucleotide sequence of SEQ ID No. 6 between positions 1 and 188, a 358 promoter, a promoter comprising the sequence of SEQ ID No. 1 between positions 447 and 1061 and a promoter comprising the sequence of SEQ ID No. 1 between positions 447 and 1061 in which TGCAG between positions 935 and 939 is changed to TTAGG.

15. The process of claim 14, in which said first gene does not comprise an intron.

16. The process of claim 12, wherein said male-fertile parent plants comprise said second gene involved in the regulation of anthocyanin biosynthesis in the cells of seeds that is functionally expressed in the seeds in said foreign DNA, and wherein said male-sterile parent plants do not contain a gene that is functionally expressed in seeds which encodes an active regulatory protein having the same activity as the protein encoded by a functional C1 gene.

17. The process of claim 16, in which said second gene comprises a DNA encoding the C1 protein which is under control of a promoter of the B-peru gene, a promoter comprising the nucleotide sequence of SEQ ID No. 6 between positions 1 and 188, a 35S promoter, a promoter comprising the sequence of SEQ ID No. 1 between positions 447 and 1061 or a promoter comprising the sequence of SEQ ID No. 1 between positions 447 and 1061 in which TGCAG between positions 935 and 939 is changed to TTAGG.

18. The process of claim 12, wherein said male-fertile parent plants comprise said first gene and said second gene in said foreign DNA, and wherein said male-sterile parent plants do not contain 1) a gene that is functionally expressed in seeds which encodes an active regulatory protein having the same activity as the protein encoded by a functional R or B gene, and 2) a gene that is functionally expressed in seeds which encodes an active regulatory protein having the same activity as the protein encoded by a functional C1 gene.

19. The process of claim 18, in which said first gene comprises a DNA encoding the B-peru protein under the control of a promoter of the B-peru gene, a promoter comprising the nucleotides sequence of SEQ ID No. 6 between positions 1 and 188, a 35S promoter, a promoter comprising the sequence of SEQ ID No. 1 between positions 447 and 1061 or a promoter comprising the sequence of SEQ ID No. 1 between positions 447 and 1061 in which TGCAG between positions 935 and 939 is changed to TTAGG; and in which said second gene comprises a DNA encoding the C1 protein which is under the control of a promoter of the B-peru gene, a promoter comprising the nucleotide sequence of SEQ ID No. 6 between positions 1 and 188, a 35S promoter, a promoter comprising the sequence of SEQ ID No. 1 between positions 447 and 1061 and a promoter comprising the sequence of SEQ ID No. 1 between positions 447 and 1061 in which TGCAG between positions 935 and 939 is changed to TTAGG.

20. The process of claim 1, in which said anthocyanin regulatory gene is selected from the group of a C1 or C1-S gene having a nucleotide sequence corresponding to the sequence between positions 447 and 2418 of SEQ ID No. 1, a B-peru gene having a nucleotide sequence corresponding to the sequence between positions 1 and 3272 of SEQ ID No. 6, and the Eco-SalI fragment having a length of about 4000 bp of pCOL13 or a combination thereof which is functional for conditioning and regulating anthocyanin biosynthesis in seeds.

21. The process of claim 20, in which said anthocyanin regulatory gene does not comprise any introns.

22. A kit for maintaining a line of male-sterile or maintainer plants, said kit comprising:
  (i) a male-sterile parent plant of said line which comprises a homozygous male-sterility genotype at a first genetic locus and which lacks an anthocyanin regulatory gene required for anthocyanin production in seeds, and
  (ii) a maintainer parent plant of said line which comprises said homozygous male-sterility genotype at said first genetic locus, and, which further comprises, at a second genetic locus which segregates independently from said first genetic locus, a foreign DNA comprising:
    a) a restorer gene, whose expression prevents phenotypic expression of said homozygous male-sterility genotype, and
    b) at least one anthocyanin regulatory gene involved in the regulation of anthocyanin biosynthesis in the cells of seeds of said plant which is capable of producing anthocyanin at least in the seeds of said plant so that anthocyanin production in the seeds is visible externally;
wherein said foreign DNA is heterozygous at said second genetic locus, and, wherein said male-sterile and male-fertile parent plant can be crossed to produce, on said male-sterile plants, seeds which produce anthocyanin, said anthocyanin being produced only in seeds comprising said at least one anthocyanin regulatory gene in said foreign DNA.

23. The kit of claim 22 in which said anthocyanin regulatory gene in said foreign DNA is expressed at least in the aleurone of seeds.

24. The kit of claim 22, in which said first genetic locus is a foreign genetic locus and comprises a male-sterility gene which, if present in the plant in the absence of said restorer genotype, would render the plant male-sterile, and wherein said male-sterility gene is homozygous at said first genetic locus.

25. The kit of claim 24 wherein said male-sterility genotype at said first enetic locus comprises a foreign DNA which comprises a male-sterility gene comprising:
  1) a male-sterility DNA encoding an RNA, protein or polypeptide which, when produced or overproduced in a stamen cell, significantly disturbs the metabolism, functioning and/or development of said cell, and, 2) a sterility promoter capable of directing expression of said male-sterility DNA selectively in the stamen cells of the plant; the male-sterility DNA being in the same transcriptional unit as, and under the control of, the sterility promoter;

and in which said restorer genotype at said second genetic locus comprises a foreign DNA which comprises a restorer gene which comprises:

1) a fertility-restorer DNA encoding a restorer RNA, protein or polypeptide which, when expressed in the same cell as said male-sterility gene, prevents the phenotypic expression of said male-sterility gene, and, 2) a restorer promoter capable of directing expression of said fertility-restorer DNA at least in the same cells in which said male-sterility gene is expressed, so that the phenotypic expression of said male-sterility gene is prevented; said fertility-restorer DNA being in the same transcriptional unit as, and under the control of, said restorer promoter.

26. The kit of claim 24, wherein said male-sterility DNA encodes a barnase and said fertility-restorer DNA encodes a barstar.

27. The kit of claim 24, wherein said sterility promoter is a TA29 promoter or a CA55 promoter.

28. The kit of claim 24, in which said sterility promoter is a PT72, PT42 or PE1 promoter.

29. The kit of claim 24, in which said restorer promoter is identical to said sterility promoter.

30. The kit of claim 29, in which said restorer promoter is a TA29 promoter or a CA55 promoter.

31. The kit of claim 23, in which said first genetic locus in an endogenous male-sterility locus, comprising a recessive allele in homozygous condition, and in which said restorer gene is the dominant allele at said endogenous male-sterility locus.

32. The kit of claim 23, in which said male-sterile parent plant contains a first anthocyanin regulatory gene involved in the regulation of anthocyanin biosynthesis in the cells of seeds that is functionally expressed in the seeds and said maintainer parent plant contains a second anthocyanin regulatory gene which when present with said first anthocyanin regulatory gene in the genome of a plant is capable of conditioning the production of anthocyanin in the seeds which is visible externally.

33. The kit of claim 23, wherein said at least one anthocyanin regulatory gene is selected from the group of a first gene that is expressed in seeds to produce a first active regulatory protein having the same activity as the protein encoded by a functional R or B gene, and a second gene that is expressed in seeds to produce a second active regulatory protein having the same activity as the protein encoded by a functional C1 gene.

34. The kit of claim 33, wherein said maintainer parent plant comprises said first gene in said foreign DNA, and said male-sterile parent plant does not contain a gene that is functionally expressed in the seeds which encodes an active regulatory protein having the same activity as the protein encoded by a functional R or B gene.

35. The kit of claim 34, in which said first gene comprises a DNA encoding a B-peru protein which is under the control of a promoter of the B-peru gene, a promoter comprising the nucleotide sequence of SEQ ID No. 6 between positions 1 and 188, a 35S promoter, a promoter comprising the sequence of SEQ ID No. 1 between positions 447 and 1061 and a promoter comprising the sequence of SEQ ID No. 1 between positions 447 and 1061 in which TGCAG between positions 935 and 939 is changed to TTAGG.

36. The kit of claim 35, in which said first gene does not comprise an intron.

37. The kit of claim 33, wherein said maintainer parent plant comprises said second gene in said foreign DNA, and said male-sterile parent plants do not contain a gene that is functionally expressed in seeds which encodes an active regulatory protein having the same activity as the protein encoded by a functional C1 gene.

38. The kit of claim 37, in which said second gene comprises a DNA encoding the C1 protein which is under control of a promoter of the B-peru gene, a promoter comprising the nucleotide sequence of SEQ ID No. 6 between positions 1 and 188, a 35S promoter, a promoter comprising the sequence of SEQ ID No. 1 between positions 447 and 1061 or a promoter comprising the sequence of SEQ ID No. 1 between positions 447 and 1061 in which TGCAG between positions 935 and 939 is changed to TTAGG.

39. The kit of claim 33, wherein said maintainer parent plant comprises said first gene and said second gene in said foreign DNA, and said male-sterile parent plants does not contain 1) a gene that is functionally expressed in seeds which encodes an active regulatory protein having the same activity as the protein encoded by a functional R or B gene, and 2) a gene that is functionally expressed in seeds which encodes an active regulatory protein having the same activity as the protein encoded by a functional C1 gene.

40. The kit of claim 39, in which said first gene comprises a DNA encoding the B-peru protein under the control of a promoter of the B-peru gene, a promoter comprising the nucleotides sequence of SEQ ID No. 6 between positions 1 and 188, a 35S promoter, a promoter comprising the sequence of SEQ ID No. 1 between positions 447 and 1061 or a promoter comprising the sequence of SEQ ID No. 1 between positions 447 and 1061 in which TGCAG between positions 935 and 939 is changed to TTAGG; and in which said second gene comprises a DNA encoding the C1 protein which is under the control of a promoter of the B-peru gene, a promoter comprising the nucleotide sequence of SEQ ID No. 6 between positions 1 and 188, a 35S promoter, a promoter comprising the sequence of SEQ ID No. 1 between positions 447 and 1061 and a promoter comprising the sequence of SEQ ID No. 1 between positions 447 and 1061 in which TGCAG between positions 935 and 939 is changed to TTAGG.

41. The kit of claim 23, in which said anthocyanin regulatory gene is selected from the group of a C1 or C1-S gene having a nucleotide sequence corresponding to the sequence between positions 447 and 2418 of SEQ ID No. 1, a B-peru gene having a nucleotide sequence corresponding to the sequence between positions 1 and 3272 of SEQ ID No. 6, and the Eco-SalI fragment having a length of about 4000 bp of pCOL13 or a combination thereof which is functional for conditioning and regulating anthocyanin biosynthesis in seeds.

42. The kit of claim 41 in which said anthocyanin regulatory gene does not comprise any introns.

43. The process of claim 1, in which said male-sterile parent plants and said male fertile parent plants are plants of the same species selected from the group of corn, wheat and rice.

44. The kit of claim 23, in which said male-sterile parent plant and said maintainer parent plant are plants of the same species selected from the group of corn, wheat and rice.

45. A male-fertile parent plant for maintaining a male-sterile line of a plant comprising male-sterile parent plants which comprise a homozygous male-sterility genotype at a first genetic locus and which lack a functional anthocyanin regulatory gene required for anthocyanin production in seeds; wherein said male-fertile parent plant comprises said homozygous male-sterility genotype at said first genetic locus, and further comprises, at a second genetic locus which segregates independently from said first genetic locus, a foreign DNA comprising:

a) a restorer gene, whose expression of which prevents the phenotypic expression of said homozygous male-sterility genotype, to render said plant male-fertile, and
  b) at least one anthocyanin regulatory gene involved in the regulation of anthocyanin biosynthesis in the cells of seeds of said plant which is capable of producing anthocyanin at least in the seeds of said plant, so that anthocyanin production in the seeds is visible externally;

wherein said foreign DNA is heterozygous at said second genetic locus, and, wherein said male-fertile parent plant can be crossed to said male-sterile parent plants to produce, on said male-sterile plants, seeds which produce anthocyanin, said anthocyanin being produced only in seeds containing said at least one anthocyanin regulatory gene in said foreign DNA.

46. The plant of claim 45, in which said anthocyanin regulatory gene is capable of producing anthocyanin at least in the aleurone of seeds.

47. The plant of claim 45, in which said first genetic locus is a foreign genetic locus and comprises a male-sterility gene which, if present in the plant in the absence of said restorer genotype, would render the plant male-sterile, and wherein said male-sterility gene is homozygous at said first genetic locus.

48. The plant of claim 47, in which said first genetic locus is homozygous for a foreign DNA which comprises a male-sterility gene comprising:

(1) a male-sterility DNA encoding an RNA, protein or polypeptide which, when produced or overproduced in a stamen cell, significantly disturbs the metabolism, functioning and/or development of said cell, and,
  (2) a sterility promoter capable of directing expression of said male-sterility DNA selectively in the stamen cells of the plant; said male-sterility DNA being in the same transcriptional unit as, and under the control of, said sterility promoter, and in which said restorer gene at said second genetic locus comprises at least:

(1) a fertility-restorer DNA encoding a restorer RNA, protein or polypeptide which, when expressed in the same cell as said male-sterility gene, prevents the phenotypic expression of said male-sterility gene, and,
  (2) a restorer promoter capable of directing expressing of said fertility-restorer DNA at least in the same cells as those in which said male-sterility gene is prevented; said fertility-restorer DNA being in the same transcriptional unit as, and under the control of, said restorer promoter.

49. The plant of claim 48, wherein said male-sterility DNA encodes a barnase and said fertility-restorer DNA encodes a barstar.

50. The plant of claim 48, in which said sterility promoter is a TA29 promoter or a CA55 promoter.

51. The plant of claim 48 in which said sterility promoter is a PT72, PT42 or PE1 promoter.

52. The plant of claim 48, in which said restorer promoter is identical to said sterility promoter.

53. The plant of claim 52, in which said restorer promoter is a TA29 promoter or a CA55 promoter.

54. The plant of claim 18, in which said first genetic locus is an endogenous male-sterility locus comprising a recessive allele in homozygous condition, and in which said restorer gene is the dominant allele at said endogenous male-sterility locus.

55. The plant of claim 45, wherein said at least one anthocyanin regulatory gene is selected from the group of a first gene that is expressed in seeds to produce a first active regulatory protein having the same activity as the protein encoded by a functional R or B gene, and a second gene that is expressed in seeds to produce a second active regulatory protein having the same activity as the protein encoded by a functional C1 gene.

56. The plant claim 55, which comprises said first gene in said foreign DNA, and which does not otherwise contain a gene that is functionally expressed in the seeds which encodes an active regulatory protein having the same activity as the protein encoded by a functional R or B gene.

57. The plant of claim 56 in which said first gene comprises a DNA encoding a B-peru protein which is under the control of a promoter of the B-peru gene, a promoter comprising the nucleotide sequence of SEQ ID No. 6 between positions 1 and 188, a 356 promoter, a promoter comprising the sequence of SEQ ID No. 1 between positions 447 and 1061 or a promoter comprising the sequences of SEQ ID No. 1 between positions 447 and 1061 in which TGCAG between positions 935 and 939 is changed to TTAGG.

58. The plant of claim 57, in which said first gene does not comprise an intron.

59. The plant of claim 55, which comprises said second gene in said foreign DNA, and which plant does not otherwise contain a gene that is functionally expressed in seeds which encodes an active regulatory protein having the same activity as the protein encoded by a functional C1 gene.

60. The plant of claim 59, in which said second gene comprises a DNA encoding the C1 protein which is under control of a promoter of the B-peru gene, a promoter comprising the nucleotide sequence of SEQ ID No. 6 between positions 1 and 188, a 358 promoter, a promoter comprising the sequence of SEQ ID No. 1 between positions 447 and 1061 in which TGCAG between positions 935 and 939 is changed to TTAGG.

61. The plant of claim 55, which comprises said first gene and said second gene in said foreign DNA, and which plant does not otherwise contain 1) a gene that is functionally expressed in seeds which encodes an active regulatory protein having the same activity as the protein encoded by a functional R or B gene, and 2) a gene that is functionally expressed in seeds which encodes an active regulatory protein having the same activity as the protein encoded by a functional C1 gene.

62. The plant of claim 61, in which said first gene comprises a DNA encoding the B-peru protein under the control of a promoter of the B-peru gene, a promoter comprising the nucleotide sequence of SEQ ID No. 6 between positions 1 and 188, a 358 promoter, a promoter comprising the sequence of SEQ ID No. 1 between positions 447 and 1061, or a promoter comprising the sequence of SEQ ID No. 1 between positions 447 and 1061 in which TGCAG between positions 938 and 939 is changed to TTAGG; and in which said second gene comprises a DNA encoding the C1 protein which is under the control of a promoter of the B-peru gene, a promoter comprising the nucleotide sequence of SEQ ID No. 6 between positions 1 and 188, a 35S promoter, a promoter comprising the sequence of SEQ ID No. 1 between positions 447 and 1061, or a promoter comprising the sequence of SEQ ID No. 1 between positions 447 and 1061 in which TGCAG between positions 935 and 939 is changed to TTAGG.

63. The plant of claim 45, in which said anthocyanin regulatory gene is selected from the group of a C1 or C1-S gene having a nucleotide sequence corresponding to the sequence between positions 447 and 2418 of SEQ ID No. 1, a B-peru gene having a nucleotide sequence corresponding to the sequence between positions 1 and 3272 of SEQ ID No. 6, and the Eco-SalI fragment having a length of about 4000 bp of pCOL13 or a combination thereof which is functional for conditioning and regulating anthocyanin biosynthesis in seeds.

64. The plant of claim 63, in which said anthocyanin regulatory gene does not comprise an intron.

65. The plant of claim 45, which is selected from the group consisting of corn, wheat and rice.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 4059 base pairs
      (B) TYPE: nucleic acid
      (C) STRANDEDNESS: double
      (D) TOPOLOGY: linear (ii) MOLECULE TYPE: DNA (genomic)

(vi) ORIGINAL SOURCE:
      (A) ORGANISM: C1 gene of Zea mays (ix) FEATURE:
      (A) NAME/KEY: -
      (B) LOCATION: 279..284
      (D) OTHER INFORMATION: /label= HpaI (ix) FEATURE:
      (A) NAME/KEY: -
      (B) LOCATION: 447..452
      (D) OTHER INFORMATION: /label= EcoRI (ix) FEATURE:
      (A) NAME/KEY: -
      (B) LOCATION: 1735..1740
      (D) OTHER INFORMATION: /label= AatII (ix) FEATURE:
      (A) NAME/KEY: -
      (B) LOCATION: 1505..1510
      (D) OTHER INFORMATION: /label= EcoRI (ix) FEATURE:
      (A) NAME/KEY: -
      (B) LOCATION: 2081..2086
      (D) OTHER INFORMATION: /label= XhoI (ix) FEATURE:
      (A) NAME/KEY: -
      (B) LOCATION: 2418..2430
      (D) OTHER INFORMATION: /label= SfiI (ix) FEATURE:
      (A) NAME/KEY: -
      (B) LOCATION: 2669..2674
      (D) OTHER INFORMATION: /label= SnaBI (ix) FEATURE:
  (A) NAME/KEY: -
  (B) LOCATION: 2634..2639
  (D) OTHER INFORMATION: /label= SnaBI (ix) FEATURE:
  (A) NAME/KEY: -
  (B) LOCATION: 3008..3013
  (D) OTHER INFORMATION: /label= HpaI (ix) FEATURE:
  (A) NAME/KEY: -
  (B) LOCATION: 1..1077
  (D) OTHER INFORMATION: /label= PC1
      /note= "region containing promoter of C1 gene"

(ix) FEATURE:
  (A) NAME/KEY: -
  (B) LOCATION: 1078..2134
  (D) OTHER INFORMATION: /label= C1
      /note= "coding region of C1 gene"

(ix) FEATURE:
  (A) NAME/KEY: -
  (B) LOCATION: 2135..2430
  (D) OTHER INFORMATION: /label= 3'C1
      /note= "region containing polyadenylation signal of C1 gene"

(ix) FEATURE:
  (A) NAME/KEY: -
  (B) LOCATION: 1033..1038
  (D) OTHER INFORMATION: /label= TATA-Box (ix) FEATURE:
  (A) NAME/KEY: -
  (B) LOCATION: 1061..1062
  (D) OTHER INFORMATION: /label= transcript-init
      /note= "transcription initiation site"

(ix) FEATURE:
  (A) NAME/KEY: intron
  (B) LOCATION: 1211..1299

(ix) FEATURE:
  (A) NAME/KEY: intron
  (B) LOCATION: 1430..1575

(ix) FEATURE:
  (A) NAME/KEY: -
  (B) LOCATION: 935..939
  (D) OTHER INFORMATION: /label= C1-S
      /note= "TGCAG sequence (in C1 gene) which in the C1-S
      sequence is changed to TTAGG"

(xi) SEQUENCE DESCRIPTION: SEQ ID NO:1:

```
TATCAACCTC CTGTGTTATT TTTAGTGACG GTTTCTTAAA AAACACCACT AGAAATCGTA      60

TTTTTATAGG TGGTTCCTTA AGAAAACTGC ATGCAGAAAT CCATGACGGT TTTCTTAAGG     120

AACCGTATGT AGAAATACGA TTTCTAGTGA CGATCTTCTT AAGGAAACCA CCACTAAAAA     180

TTATTTTTAT CCTTAATTTT CGAGTTTTTC AAACGATCTC GTATGATGAA ACCATCAAAA     240

TAAAAGTTGT ACATCTCTAA AAGTTATGAA AATTTGTAGT TAACAACTTT TTTATTTGAA     300

CTCATTTTGG TTCTCAAAAA TTGCATCTAA ATTTGTCAAA TTTAAAATTC AAATTTTCCA     360

AACGACCTCG GATGAAAAAA GTGTCAAAAT GAAAGTTGTA GAACTTCAAA AGTTATTCAA     420

CTTTGTAGTC GACTATCTTT TTATTTGAAT TCGCTTACGG TCTCAAACAA GCAATTTACA     480

CTCAGTTGGT TGTAATATGT GGACAATAAA ACTACAAACT AGACACAAAT CATACCATAG     540

ACGGAGTGGT AGCAGAGGGT ACGCGCGAGG GTGAGATAGA GGATTCTCCT AAAATAAATG     600

CACTTTAGAT GGGTAGGGTG GGGTGAGGCC TCTCCTAAAA TGAAACTCGT TTAATGTTTC     660

TAAAAATAGT TTTCACTGGT GATCCTTAGT TACTGGCATG TAAAAATGAT GATTTCTACT     720
```

```
GTCTCTCATA TGGACGGTTA TAAAAAATAC CATTATATTG AAAATAGGTC TCTGCTGCTA      780
CACTCGCCCT CATAGCAGAT CATGCATGCA CGCATCATTC GATCAGTTTT CGTTCTGATG      840
CAGTTTTCGA TAAATGCCAA TTTTTTAACT GCATACGTTG CCCTTGCTCA GCACCAGCAC      900
AGCAGTGTCG TGTCGTCCAT GCATGCACTT TAGGTGCAGT GCAGGGCCTC AACTCGGCCA      960
CGTAGTTAGC GCCACTGCTA CAGATCGAGG CACCGGTCAG CCGGCCACGC ACGTCGACCG     1020
CGCGCGTGCA TTTAAATACG CCGACGACGG AGCTTGATCG ACGAGAGAGC GAGCGCGATG     1080
GGGAGGAGGG CGTGTTGCGC GAAGGAAGGC GTTAAGAGAG GGGCGTGGAC GAGCAAGGAG     1140
GACGATGCCT TGGCCGCCTA CGTCAAGGCC CATGGCGAAG GCAAATGGAG GGAAGTGCCC     1200
CAGAAAGCCG GTAAAACTAG CTAGTCTTTT TATTTCATTT TGGGATCATA TATATACCCC     1260
CGAGGCAAGA CCGGAGGACG ATCACGTGTG TGGGTGCAGG TTTGCGTCGG TGCGGCAAGA     1320
GCTGCCGGCT GCGGTGGCTG AACTACCTCC GGCCCAACAT CAGGCGCGGC AACATCTCCT     1380
ACGACGAGGA GGATCTCATC ATCCGCCTCC ACAGGCTCCT CGGCAACAGG TCTGTGCAGT     1440
GGCCAGTGGT GGGCTAGCTT ATTACACGAG CTGACGACGA GGCGATCGAT CGAGCGTCTG     1500
CTGCGAATTC ATCTGTTCCG GTGTCGGCCG TGTGAGAGTG AGCTCATTCA TATGTACATG     1560
CGTGTTGGCG CGCAGGTGGT CGCTGATTGC AGGCAGGCTG CCTGGCCGAA CAGACAATGA     1620
AATCAAGAAC TACTGGAACA GCACGCTGGG CCGGAGGGCA GGCGCCGGCG CCGGCGCCGG     1680
CGGCAGCTGG GTCGTCGTCG CGCCGGACAC CGGCTCGCAC GCCACCCCGG CCGCGACGTC     1740
GGGCGCCTGC GAGACCGGCC AGAATAGCGC CGCTCATCGC GCGGACCCCG ACTCAGCCGG     1800
GACGACGACG ACCTCGGCGG CGGCGGTGTG GGCGCCCAAG GCCGTGCGGT GCACGGGCGG     1860
ACTCTTCTTC TTCCACCGGG ACACGACGCC GGCGCACGCG GGCGAGACGG CGACGCCAAT     1920
GGCCGGTGGA GGTGGAGGAG GAGGAGGAGA AGCAGGGTCG TCGGACGACT GCAGCTCGGC     1980
GGCGTCGGTA TCGCTTCGCG TCGGAAGCCA CGACGAGCCG TGCTTCTCCG GCGACGGTGA     2040
CGGCGACTGG ATGGACGACG TGAGGGCCCT GGCGTCGTTT CTCGAGTCCG ACGAGGACTG     2100
GCTCCGCTGT CAGACGGCCG GGCAGCTTGC GTAGACAACA AGTACACGTA TAGATGTCCA     2160
ATAAGCACGA GGCCCGCGAG CCCGCGACGA AGCCCGCTTT TTGGGCCCGG TCCGAGCCCG     2220
GCACGGCCCG GTTATATGCA GACCCGGGCC GGCCCGGCAC GAATAAGCGG GCCGGGCTCG     2280
GACAGGAAAT TAGGCACGGT GAGCTAGCCC GGCACGGCCC GTTTAGGTCT AAGCCCGTTA     2340
AGCCCGTTTT TTTACACTAA AACGTGCTTC TCGGCCCGCA TAGCCCGCTT CTCGGCCCGC     2400
TTTTTTCGTG CTAAACGGGC CGGCCCGGCC CGGTTTAGGC CCGTTGCGGG CCGGGCTCGG     2460
ACAGGAAATT GAGCCCGCGT GCTTAGCCGG CCCGGCCCGG TTTTTTAATC GTGCCTGGCG     2520
GGCCAGGCCC AAAACGGGCC GGGCTTCACC GGGCCCGGGC CGGACCGGGC CGGGCGGCCC     2580
GTTTGGACAT CTCTAAGTAC ACGTATGGAG GAGAATATAT ATATAGTCAT GCGTACGTAT     2640
AGATTTTTTC ATCCGATCCC AACAGAAATA CGTATGAAAA TGCTCTTCGT TCTTTTTCAT     2700
TTATCATATC TATACTATAC TTAAAACACC AGTTTCAACG GTCGTCATGC GTCATTTTTT     2760
TACAAATAAC CCCTCACAGC TATTTCAAAT TAATCCGCTG CACGTCTATA GATGCCAAAC     2820
GACGCCCAAC ACGGGCTAGA TGCACGCGGG CCACAACTAT GGCACAGGCA CGTCATGCCG     2880
GCCTGCTAAC TGTGTCGGGC TAGCCCGTTA GCCCGTCGAT CCATTTAATT AAATTAGCGT     2940
AACGACGCCC GACACGGGCT AGATGCACGT GGGCCACAAC TATGGCACAT GCACGTCATG     3000
CCGGCCTGTT AACTGTGTCG GGCCAGTCTG TTAGCCCATT GATCCATTTA ATTAAATCAG     3060
CGTAAAATGT TAAAAACGGT GCAGGAGGTG GGGTTCGAAC CCATACCCTG ATGGAAGAAG     3120
```

```
GGCGGGAGAC ACTGGGTGAA ACTGTCTAAC CAGTAGAATA TCTATCACGC TAAGATGTTT      3180

TTAATATTGA ATATAAATTG TATATAAGCA TATAAGTTTT TTTGTAAAAT AAAAAATAAT      3240

CGTGTCGGGC CGGGCCATCA CTACTGGCCG AGGCTACAAC CCAAGCACGA CACGACGTTC      3300

TTGGCTCTTG CAAGCATTAG GTCGTTTCTG AGACCATATT GGCGCAATGG ACTACATGAT      3360

GTTTGGGGTT GCTGAATTGA ATGGAGCAGC AATAATTTGT CACACTAACA GCAAAATGAA      3420

AGGTTATTTG TTGGTTTTAA ACGTTAGTAA TTGCTACGAA GTAGCATAAT TTATATGGAG      3480

CGCATCCAGT TTTTATTGAT GCCTGACTTT AGCAATCACT CCATATTTTG ATCTATCTTT      3540

TTTATAAGTT TGACTTCATG GGACTTATTT TAGAACTTGA TCTCACAAAC TTTCTCTTAT      3600

TTTGTCTCTA TATGATGAAA TTGTGTCATT TTATAATCTT TGTTCATTCA GTCAATCGTT      3660

GTGAACTCTC TTCTAATCAC TCACTTCATT AGTTGTGTTG TACCAAGACA TATTTGCATA      3720

GAGTAAACAA TAACATCAGT TAGCCAAATC AAAAAATATA TTATACAGAG AGCGGAGACA      3780

ATCAAATAAA AAATCTTGAA ATTTTTTTAA TGGATAGTTT ACGTGGGTAT TGTTGTAAGC      3840

CGTCGCAACG CACGGGCAAC CGACTAGTTT TAGTTTATAA ATTAATAAAC GTACGACAAA      3900

TATTAAGAAC GCCACCTTTC CATGCCTACG CGCGCGTGAG ACACGACCGG GGCACGTCAG      3960

ACGTGTGCCC CTGTTGTATA ATTTATTTAC TTTTTAATGA CTATGTGCTG TTGGTTGCCG      4020

TTGGCTTCAT CGTGTTCGTA GCCATGCATA AATCCAGCG                            4059
```

(2) INFORMATION FOR SEQ ID NO:2:

(i) SEQUENCE CHARACTERISTICS:
        (A) LENGTH: 4896 base pairs
        (B) TYPE: nucleic acid
        (C) STRANDEDNESS: double
        (D) TOPOLOGY: circular (ii) MOLECULE TYPE: DNA (genomic)

(vi) ORIGINAL SOURCE:
        (A) ORGANISM: plasmid pTS256, linearized at HindIII (ix) FEATURE:
        (A) NAME/KEY: -
        (B) LOCATION: 39..317
        (D) OTHER INFORMATION: /label= 3'nos
            /note= "3' regulatory sequence containing the
            polyadenylation signal of the nopaline synthase
            gene of Agrobacterium T-DNA"

(ix) FEATURE:
        (A) NAME/KEY: -
        (B) LOCATION: 318..869
        (D) OTHER INFORMATION: /label= bar
            /note= "coding region of bar gene of Streptomyces
            hygroscopicus"

(ix) FEATURE:
        (A) NAME/KEY: -
        (B) LOCATION: 870..1702
        (D) OTHER INFORMATION: /label= P35S
            /note= "35S promoter of Cauliflower Mosaic Virus"

(ix) FEATURE:
        (A) NAME/KEY: -
        (B) LOCATION: 1740..2284
        (D) OTHER INFORMATION: /label= PTA29
            /note= "promoter of TA29 gene of Nicotiana tabacum"

(ix) FEATURE:
        (A) NAME/KEY: -
        (B) LOCATION: 2285..2557
        (D) OTHER INFORMATION: /label= barstar
            /note= "coding region of barstar gene of
            Bacillusamyloliquefacien"

(ix) FEATURE:
    (A) NAME/KEY: -
    (B) LOCATION: 2558..2879
    (D) OTHER INFORMATION: /label= 3'nos
        /note= "3' regulatory sequence containing the
        polyadenylation signal of the nopaline synthase
        gene of Agrobacterium T-DNA"

(ix) FEATURE:
    (A) NAME/KEY: -
    (B) LOCATION: 1..38
    (D) OTHER INFORMATION: /label= pUC19
        /note= "pUC19 derived sequence"

(ix) FEATURE:
    (A) NAME/KEY: -
    (B) LOCATION: 2880..4896
    (D) OTHER INFORMATION: /label= pUC19
        /note= "pUC19 derived sequence"

(ix) FEATURE:
    (A) NAME/KEY: -
    (B) LOCATION: 3004..3009
    (D) OTHER INFORMATION: /label= EcoRI (xi) SEQUENCE DESCRIPTION: SEQ ID NO:2:

```
AGCTTGCATG CCTGCAGGTC GACTCTAGAG GATCTTCCCG ATCTAGTAAC ATAGATGACA      60

CCGCGCGCGA TAATTTATCC TAGTTTGCGC GCTATATTTT GTTTTCTATC GCGTATTAAA     120

TGTATAATTG CGGGACTCTA ATCATAAAAA CCCATCTCAT AAATAACGTC ATGCATTACA     180

TGTTAATTAT TACATGCTTA ACGTAATTCA ACAGAAATTA TATGATAATC ATCGCAAGAC     240

CGGCAACAGG ATTCAATCTT AAGAAACTTT ATTGCCAAAT GTTTGAACGA TCTGCTTCGG     300

ATCCTAGACG CGTGAGATCA GATCTCGGTG ACGGGCAGGA CCGGACGGGG CGGTACCGGC     360

AGGCTGAAGT CCAGCTGCCA GAAACCCACG TCATGCCAGT TCCCGTGCTT GAAGCCGGCC     420

GCCCGCAGCA TGCCGCGGGG GGCATATCCG AGCGCCTCGT GCATGCGCAC GCTCGGGTCG     480

TTGGGCAGCC CGATGACAGC GACCACGCTC TTGAAGCCCT GTGCCTCCAG GGACTTCAGC     540

AGGTGGGTGT AGAGCGTGGA GCCCAGTCCC GTCCGCTGGT GGCGGGGGGA GACGTACACG     600

GTCGACTCGG CCGTCCAGTC GTAGGCGTTG CGTGCCTTCC AGGGGCCCGC GTAGGCGATG     660

CCGGCGACCT CGCCGTCCAC CTCGGCGACG AGCCAGGGAT AGCGCTCCCG CAGACGGACG     720

AGGTCGTCCG TCCACTCCTG CGGTTCCTGC GGCTCGGTAC GGAAGTTGAC CGTGCTTGTC     780

TCGATGTAGT GGTTGACGAT GGTGCAGACC GCCGGCATGT CCGCCTCGGT GGCACGGCGG     840

ATGTCGGCCG GGCGTCGTTC TGGGTCCATG GTTATAGAGA GAGAGATAGA TTTATAGAGA     900

GAGACTGGTG ATTTCAGCGT GTCCTCTCCA AATGAAATGA ACTTCCTTAT ATAGAGGAAG     960

GGTCTTGCGA AGGATAGTGG GATTGTGCGT CATCCCTTAC GTCAGTGGAG ATGTCACATC    1020

AATCCACTTG CTTTGAAGAC GTGGTTGGAA CGTCTTCTTT TTCCACGATG CTCCTCGTGG    1080

GTGGGGGTCC ATCTTTGGGA CCACTGTCGG CAGAGGCATC TTGAATGATA GCCTTTCCTT    1140

TATCGCAATG ATGGCATTTG TAGGAGCCAC CTTCCTTTTC TACTGTCCTT TCGATGAAGT    1200

GACAGATAGC TGGGCAATGG AATCCGAGGA GGTTTCCCGA AATTATCCTT TGTTGAAAAG    1260

TCTCAATAGC CCTTTGGTCT TCTGAGACTG TATCTTTGAC ATTTTTGGAG TAGACCAGAG    1320

TGTCGTGCTC CACCATGTTG ACGAAGATTT TCTTCTTGTC ATTGAGTCGT AAAAGACTCT    1380

GTATGAACTG TTCGCCAGTC TTCACGGCGA GTTCTGTTAG ATCCTCGATT TGAATCTTAG    1440

ACTCCATGCA TGGCCTTAGA TTCAGTAGGA ACTACCTTTT TAGAGACTCC AATCTCTATT    1500

ACTTGCCTTG GTTTATGAAG CAAGCCTTGA ATCGTCCATA CTGGAATAGT ACTTCTGATC    1560

TTGAGAAATA TGTCTTTCTC TGTGTTCTTG ATGCAATTAG TCCTGAATCT TTTGACTGCA    1620
```

```
TCTTTAACCT TCTTGGGAAG GTATTTGATC TCCTGGAGAT TGTTACTCGG GTAGATCGTC    1680

TTGATGAGAC CTGCTGCGTA GGAGCTTGCA TGCCTGCAGG TCGACTCTAG AGGATCCCCA    1740

TCTAGCTAAG TATAACTGGA TAATTTGCAT TAACAGATTA AATATAGTGC CAAACAAGAA    1800

GGGACAATTG ACTTGTCACT TTATGAAAGA TGATTCAAAC ATGATTTTTT ATGTACTAAT    1860

ATATACATCC TACTCGAATT AAAGCGACAT AGGCTCGAAG TATGCACATT TAGCAATGTA    1920

AATTAAATCA GTTTTTGAAT CAAGCTAAAA GCAGACTTGC ATAAGGTGGG TGGCTGGACT    1980

AGAATAAACA TCTTCTCTAG CACAGCTTCA TAATGTAATT TCCATAACTG AAATCAGGGT    2040

GAGACAAAAT TTTGGTACTT TTTCCTCACA CTAAGTCCAT GTTTGCAACA AATTAATACA    2100

TGAAACCTTA ATGTTACCCT CAGATTAGCC TGCTACTCCC CATTTTCCTC GAAATGCTCC    2160

AACAAAAGTT AGTTTTGCAA GTTGTTGTGT ATGTCTTGTG CTCTATATAT GCCCTTGTGG    2220

TGCAAGTGTA ACAGTACAAC ATCATCACTC AAATCAAAGT TTTTACTTAA AGAAATTAGC    2280

TACCATGAAA AAAGCAGTCA TTAACGGGGA ACAAATCAGA AGTATCAGCG ACCTCCACCA    2340

GACATTGAAA AAGGAGCTTG CCCTTCCGGA ATACTACGGT GAAAACCTGG ACGCTTTATG    2400

GGATTGTCTG ACCGGATGGG TGGAGTACCC GCTCGTTTTG GAATGGAGGC AGTTTGAACA    2460

AAGCAAGCAG CTGACTGAAA ATGGCGCCGA GAGTGTGCTT CAGGTTTTCC GTGAAGCGAA    2520

AGCGGAAGGC TGCGACATCA CCATCATACT TTCTTAATAC GATCAATGGG AGATGAACAA    2580

TATGGAAACA CAAACCCGCA AGCTTGGTCT AGAGGATCCG AAGCAGATCG TTCAAACATT    2640

TGGCAATAAA GTTTCTTAAG ATTGAATCCT GTTGCCGGTC TTGCGATGAT TATCATATAA    2700

TTTCTGTTGA ATTACGTTAA GCATGTAATA ATTAACATGT AATGCATGAC GTTATTTATG    2760

AGATGGGTTT TTATGATTAG AGTCCCGCAA TTATACATTT AATACGCGAT AGAAAACAAA    2820

ATATAGCGCG CAAACTAGGA TAAATTATCG CGCGCGGTGT CATCTATGTT ACTAGATCGG    2880

GAAGATCCCC GGGTACCGAG CTCGAATTCT GATCAGGCCA ACGCGCGGGG AGAGGCGGTT    2940

TGCGTATTGG GCGCTCTTCC GCTTCCTCGC TCACTGACTC GCTGCGCTCG GTCGTTCGGC    3000

TGCGGCGAGC GGTATCAGCT CACTCAAAGG CGGTAATACG GTTATCCACA GAATCAGGGG    3060

ATAACGCAGG AAAGAACATG TGAGCAAAAG GCCAGCAAAA GGCCAGGAAC CGTAAAAAGG    3120

CCGCGTTGCT GGCGTTTTTC CATAGGCTCC GCCCCCCTGA CGAGCATCAC AAAAATCGAC    3180

GCTCAAGTCA GAGGTGGCGA AACCCGACAG GACTATAAAG ATACCAGGCG TTTCCCCCTG    3240

GAAGCTCCCT CGTGCGCTCT CCTGTTCCGA CCCTGCCGCT TACCGGATAC CTGTCCGCCT    3300

TTCTCCCTTC GGGAAGCGTG GCGCTTTCTC AATGCTCACG CTGTAGGTAT CTCAGTTCGG    3360

TGTAGGTCGT TCGCTCCAAG CTGGGCTGTG TGCACGAACC CCCCGTTCAG CCCGACCGCT    3420

GCGCCTTATC CGGTAACTAT CGTCTTGAGT CCAACCCGGT AAGACACGAC TTATCGCCAC    3480

TGGCAGCAGC CACTGGTAAC AGGATTAGCA GAGCGAGGTA TGTAGGCGGT GCTACAGAGT    3540

TCTTGAAGTG GTGGCCTAAC TACGGCTACA CTAGAAGGAC AGTATTTGGT ATCTGCGCTC    3600

TGCTGAAGCC AGTTACCTTC GGAAAAAGAG TTGGTAGCTC TTGATCCGGC AAACAAACCA    3660

CCGCTGGTAG CGGTGGTTTT TTTGTTTGCA AGCAGCAGAT TACGCGCAGA AAAAAGGAT    3720

CTCAAGAAGA TCCTTTGATC TTTTCTACGG GTCTGACGC TCAGTGGAAC GAAAACTCAC    3780

GTTAAGGGAT TTTGGTCATG AGACTCGAGC CAAAAAGGAT CTTCACCTAG ATCCTTTTAA    3840

ATTAAAAATG AAGTTTTAAA TCAATCTAAA GTATATATGA GTAACCTTGG TCTGACAGTT    3900

ACCAATGCTT AATCAGTGAG GCACCTATCT CAGCGATCTG TCTATTTCGT TCATCCATAG    3960

TTGCCTGACT CCCCGTCGTG TAGATAACTA CGATACGGGA GGGCTTACCA TCTGGCCCCA    4020
```

```
GTGCTGCAAT GATACCGCGA GACCCACGCT CACCGGCTCC AGATTTATCA GCAATAAACC    4080

AGCCAGCCGG AAGGGCCGAG CGCAGAAGTG GTCCTGCAAC TTTATCCGCC TCCATCCAGT    4140

CTATTAATTG TTGCCGGGAA GCTAGAGTAA GTAGTTCGCC AGTTAATAGT TTGCGCAACG    4200

TTGTTGCCAT TGCTACAGGC ATCGTGGTGT CACGCTCGTC GTTTGGTATG GCTTCATTCA    4260

GCTCCGGTTC CCAACGATCA AGGCGAGTTA CATGATCCCC CATGTTGTGC AAAAAAGCGG    4320

TTAGCTCCTT CGGTCCTCCG ATCGTTGTCA GAAGTAAGTT GGCCGCAGTG TTATCACTCA    4380

TGGTTATGGC AGCACTGCAT AATTCTCTTA CTGTCATGCC ATCCGTAAGA TGCTTTTCTG    4440

TGACTGGTGA GTACTCAACC AAGTCATTCT GAGAATAGTG TATGCGGCGA CCGAGTTGCT    4500

CTTGCCCGGC GTCAATACGG GATAATACCG CGCCACATAG CAGAACTTTA AAAGTGCTCA    4560

TCATTGGAAA ACGTTCTTCG GGGCGAAAAC TCTCAAGGAT CTTACCGCTG TTGAGATCCA    4620

GTTCGATGTA ACCCACTCGT GCACCCAACT GATCTTCAGC ATCTTTTACT TTCACCAGCG    4680

TTTCTGGGTG AGCAAAAACA GGAAGGCAAA ATGCCGCAAA AAAGGGAATA AGGGCGACAC    4740

GGAAATGTTG AATACTCATA CTCTTCCTTT TTCAATATTA TTGAAGCATT TATCAGGGTT    4800

ATTGTCTCAT GAGCGGATAC ATATTTGAAT GTATTTAGAA AAATAAACAA ATAGGGGTTC    4860

CGCGCACATT TCCCCGAAAA GTGCCACCTG ACGTCA                              4896
```

(2) INFORMATION FOR SEQ ID NO:3:

(i) SEQUENCE CHARACTERISTICS:
        (A) LENGTH: 3544 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: EcoRI-HindIII region of plasmid pTS200

(ix) FEATURE:
        (A) NAME/KEY: -
        (B) LOCATION: 3227..3504
        (D) OTHER INFORMATION: /label= 3'nos
            /note= "3' regulatory sequence containing the
            polyadenylation signal of the nopaline synthase
            gene of Agrobacterium T-DNA"

(ix) FEATURE:
        (A) NAME/KEY: -
        (B) LOCATION: 2675..3226
        (D) OTHER INFORMATION: /label= bar
            /note= "coding region of bar gene of Streptomyces
            hygroscopicus"

(ix) FEATURE:
        (A) NAME/KEY: -
        (B) LOCATION: 1841..2674
        (D) OTHER INFORMATION: /label= P35S
            /note= "35S promoter of Cauliflower Mosaic Virus"

(ix) FEATURE:
        (A) NAME/KEY: -
        (B) LOCATION: 626..1803
        (D) OTHER INFORMATION: /label= PCA55
            /note= "promoter of CA55 gene of Zea mays"

(ix) FEATURE:
        (A) NAME/KEY: -
        (B) LOCATION: 353..625
        (D) OTHER INFORMATION: /label= barstar
            /note= "coding region of barstar gene of Bacillus
            amyloliquefaciens"

(ix) FEATURE:

(A) NAME/KEY: -
(B) LOCATION: 30..352
(D) OTHER INFORMATION: /label= 3'nos
    /note= "3' regulatory sequence containing the
    polyadenylation signal of the nopaline synthase
    gene of Agrobacterium T-DNA"

(ix) FEATURE:
(A) NAME/KEY: -
(B) LOCATION: 1..6
(D) OTHER INFORMATION: /label= EcoRI (ix) FEATURE:
(A) NAME/KEY: -
(B) LOCATION: 3539..3544
(D) OTHER INFORMATION: /label= HindIII (xi) SEQUENCE DESCRIPTION: SEQ ID NO:3:

```
GAATTCGAGC TCGGTACCCG GGGATCTTCC CGATCTAGTA ACATAGATGA CACCGCGCGC      60

GATAATTTAT CCTAGTTTGC GCGCTATATT TTGTTTTCTA TCGCGTATTA AATGTATAAT     120

TGCGGGACTC TAATCATAAA AACCCATCTC ATAAATAACG TCATGCATTA CATGTTAATT     180

ATTACATGCT TAACGTAATT CAACAGAAAT TATATGATAA TCATCGCAAG ACCGGCAACA     240

GGATTCAATC TTAAGAAACT TTATTGCCAA ATGTTTGAAC GATCTGCTTC GGATCCTCTA     300

GACCAAGCTT GCGGGTTTGT GTTTCCATAT TGTTCATCTC CCATTGATCG TATTAAGAAA     360

GTATGATGGT GATGTCGCAG CCTTCCGCTT TCGCTTCACG GAAAACCTGA AGCACACTCT     420

CGGCGCCATT TTCAGTCAGC TGCTTGCTTT GTTCAAACTG CCTCCATTCC AAAACGAGCG     480

GGTACTCCAC CCATCCGGTC AGAGAATCCC ATAAAGCGTC CAGGTTTTCA CCGTAGTATT     540

CCGGAAGGGC AAGCTCCTTT TTCAATGTCT GGTGGAGGTC GCTGATACTT CTGATTTGTT     600

CCCCGTTAAT GACTGCTTTT TCATGGCTG CAGCTAGTTA GCTCGATGTA TCTTCTGTAT      660

ATGCAGTGCA GCTTCTGCGT TTTGGCTGCT TTGAGCTGTG AAATCTCGCT TTCCAGTCCC     720

TGCGTGTTTT ATAGTGCTGT ACGTTCGTGA TCGTGAGCAA ACAGGGCGTG CCTCAACTAC     780

TGGTTTGGTT GGGTGACAGG CGCCAACTAC GTGCTCGTAA CCGATCGAGT GAGCGTAATG     840

CAACATTTTT TCTTCTTCTC TCGCATTGGT TTCATCCAGC CAGGAGACCC GAATCGAATT     900

GAAATCACAA ATCTGAGGTA CAGTATTTTT ACAGTACCGT TCGTTCGAAG GTCTTCGACA     960

GGTCAAGGTA ACAAAATCAG TTTTAAATTG TTGTTTCAGA TCAAAGAAAA TTGAGATGAT    1020

CTGAAGGACT TGGACCTTCG TCCAATGAAA CACTTGGACT AATTAGAGGT GAATTGAAAG    1080

CAAGCAGATG CAACCGAAGG TGGTGAAAGT GGAGTTTCAG CATTGACGAC GAAAACCTTC    1140

GAACGGTATA AAAAGAAGC CGCAATTAAA CGAAGATTTG CCAAAAGAT GCATCAACCA      1200

AGGGAAGACG TGCATACATG TTTGATGAAA ACTCGTAAAA ACTGAAGTAC GATTCCCCAT    1260

TCCCCTCCTT TTCTCGTTTC TTTTAACTGA AGCAAAGAAT TTGTATGTAT TCCCTCCATT    1320

CCATATTCTA GGAGGTTTTG GCTTTTCATA CCCTCCTCCA TTTCAAATTA TTTGTCATAC    1380

ATTGAAGATA TACACCATTC TAATTTATAC TAAATTACAG CTTTTAGATA CATATATTTT    1440

ATTATACACT TAGATACGTA TTATATAAAA CACCTAATTT AAAATAAAAA ATTATATAAA    1500

AAGTGTATCT AAAAAATCAA AATACGACAT AATTTGAAAC GGAGGGGTAC TACTTATGCA    1560

AACCAATCGT GGTAACCCTA AACCCTATAT GAATGAGGCC ATGATTGTAA TGCACCGTCT    1620

GATTAACCAA GATATCAATG GTCAAACATA TACATGATAC ATCCAAGTCA CAGCGAAGGC    1680

AAATGTGACA ACAGTTTTTT TTACCAGAGG GACAAGGGAG AATATCTATT CAGATGTCAA    1740

GTTCCCGTAT CACACTGCCA GGTCCTTACT CCAGACCATC TTCCGGCTCT ATTGATGCAT    1800

ACCAGGAATT GATCTAGAGT CGACCTGCAG GCATGCAAGC TCCTACGCAG CAGGTCTCAT    1860
```

```
CAAGACGATC TACCCGAGTA ACAATCTCCA GGAGATCAAA TACCTTCCCA AGAAGGTTAA      1920

AGATGCAGTC AAAAGATTCA GGACTAATTG CATCAAGAAC ACAGAGAAAG ACATATTTCT      1980

CAAGATCAGA AGTACTATTC CAGTATGGAC GATTCAAGGC TTGCTTCATA AACCAAGGCA      2040

AGTAATAGAG ATTGGAGTCT CTAAAAAGGT AGTTCCTACT GAATCTAAGG CCATGCATGG      2100

AGTCTAAGAT TCAAATCGAG GATCAACAG AACTCGCCGT GAAGACTGGC GAACAGTTCA      2160

TACAGAGTCT TTTACGACTC AATGACAAGA AGAAAATCTT CGTCAACATG GTGGAGCACG      2220

ACACTCTGGT CTACTCCAAA AATGTCAAAG ATACAGTCTC AGAAGACCAA AGGGCTATTG      2280

AGACTTTTCA ACAAAGGATA ATTTCGGGAA ACCTCCTCGG ATTCCATTGC CCAGCTATCT      2340

GTCACTTCAT CGAAAGGACA GTAGAAAAGG AAGGTGGCTC CTACAAATGC CATCATTGCG      2400

ATAAAGGAAA GGCTATCATT CAAGATGCCT CTGCCGACAG TGGTCCCAAA GATGGACCCC      2460

CACCCACGAG GAGCATCGTG GAAAAAGAAG ACGTTCCAAC CACGTCTTCA AAGCAAGTGG      2520

ATTGATGTGA CATCTCCACT GACGTAAGGG ATGACGCACA ATCCCACTAT CCTTCGCAAG      2580

ACCCTTCCTC TATATAAGGA AGTTCATTTC ATTTGGAGAG GACACGCTGA AATCACCAGT      2640

CTCTCTCTAT AAATCTATCT CTCTCTCTAT AACCATGGAC CCAGAACGAC GCCCGGCCGA      2700

CATCCGCCGT GCCACCGAGG CGGACATGCC GGCGGTCTGC ACCATCGTCA ACCACTACAT      2760

CGAGACAAGC ACGGTCAACT TCCGTACCGA GCCGCAGGAA CCGCAGGAGT GGACGGACGA      2820

CCTCGTCCGT CTGCGGGAGC GCTATCCCTG GCTCGTCGCC GAGGTGGACG GCGAGGTCGC      2880

CGGCATCGCC TACGCGGGCC CCTGGAAGGC ACGCAACGCC TACGACTGGA CGGCCGAGTC      2940

GACCGTGTAC GTCTCCCCCC GCCACCAGCG GACGGGACTG GGCTCCACGC TCTACACCCA      3000

CCTGCTGAAG TCCCTGGAGG CACAGGGCTT CAAGAGCGTG GTCGCTGTCA TCGGGCTGCC      3060

CAACGACCCG AGCGTGCGCA TGCACGAGGC GCTCGGATAT GCCCCCCGCG GCATGCTGCG      3120

GGCGGCCGGC TTCAAGCACG GGAACTGGCA TGACGTGGGT TTCTGGCAGC TGGACTTCAG      3180

CCTGCCGGTA CCGCCCCGTC CGGTCCTGCC CGTCACCGAG ATCTGATCTC ACGCGTCTAG      3240

GATCCGAAGC AGATCGTTCA AACATTTGGC AATAAAGTTT CTTAAGATTG AATCCTGTTG      3300

CCGGTCTTGC GATGATTATC ATATAATTTC TGTTGAATTA CGTTAAGCAT GTAATAATTA      3360

ACATGTAATG CATGACGTTA TTTATGAGAT GGGTTTTTAT GATTAGAGTC CCGCAATTAT      3420

ACATTTAATA CGCGATAGAA AACAAAATAT AGCGCGCAAA CTAGGATAAA TTATCGCGCG      3480

CGGTGTCATC TATGTTACTA GATCGGGAAG ATCCTCTAGA GTCGACCTGC AGGCATGCAA      3540

GCTT                                                                   3544
```

(2) INFORMATION FOR SEQ ID NO:4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: oligonucleotide 1

(xi) SEQUENCE DESCRIPTION: SEQ ID NO:4:

```
CGTTTCTCGA ATCCGACGAG G                                                  21
```

(2) INFORMATION FOR SEQ ID NO:5:

(i) SEQUENCE CHARACTERISTICS:
    (A) LENGTH: 4824 base pairs
    (B) TYPE: nucleic acid
    (C) STRANDEDNESS: double
    (D) TOPOLOGY: circular (ii) MOLECULE TYPE: DNA (genomic)

(vi) ORIGINAL SOURCE:
    (A) ORGANISM: plasmid pCOL9

(ix) FEATURE:
    (A) NAME/KEY: -
    (B) LOCATION: 396..401
    (D) OTHER INFORMATION: /label= EcoRI (ix) FEATURE:
    (A) NAME/KEY: -
    (B) LOCATION: 2367..2379
    (D) OTHER INFORMATION: /label= SfiI (ix) FEATURE:
    (A) NAME/KEY: -
    (B) LOCATION: 884..888
    (D) OTHER INFORMATION: /label= C1-S
        /note= "TGCAG (in C1) which in C1-S allele is
        replaced with TTAGG"

(xi) SEQUENCE DESCRIPTION: SEQ ID NO:5:

```
TCGCGCGTTT CGGTGATGAC GGTGAAAACC TCTGACACAT GCAGCTCCCG GAGACGGTCA      60

CAGCTTGTCT GTAAGCGGAT GCCGGGAGCA GACAAGCCCG TCAGGGCGCG TCAGCGGGTG     120

TTGGCGGGTG TCGGGCTGG CTTAACTATG CGGCATCAGA GCAGATTGTA CTGAGAGTGC      180

ACCATATGCG GTGTGAAATA CCGCACAGAT GCGTAAGGAG AAAATACCGC ATCAGGCGCC     240

ATTCGCCATT CAGGCTGCGC AACTGTTGGG AAGGGCGATC GGTGCGGGCC TCTTCGCTAT     300

TACGCCAGCT GGCGAAAGGG GGATGTGCTG CAAGGCGATT AAGTTGGGTA ACGCCAGGGT     360

TTTCCCAGTC ACGACGTTGT AAAACGACGG CCAGTGAATT CGCTTACGGT CTCAAACAAG     420

CAATTTACAC TCAGTTGGTT GTAATATGTG GACAATAAAA CTACAAACTA GACACAAATC     480

ATACCATAGA CGGAGTGGTA GCAGAGGGTA CGCGCGAGGG TGAGATAGAG GATTCTCCTA     540

AAATAAATGC ACTTTAGATG GGTAGGGTGG GGTGAGGCCT CTCCTAAAAT GAAACTCGTT     600

TAATGTTTCT AAAAATAGTT TTCACTGGTG ATCCTTAGTT ACTGGCATGT AAAAATGATG     660

ATTTCTACTG TCTCTCATAT GGACGGTTAT AAAAAATACC ATTATATTGA AAATAGGTCT     720

CTGCTGCTAC ACTCGCCCTC ATAGCAGATC ATGCATGCAC GCATCATTCG ATCAGTTTTC     780

GTTCTGATGC AGTTTTCGAT AAATGCCAAT TTTTTAACTG CATACGTTGC CCTTGCTCAG     840

CACCAGCACA GCAGTGTCGT GTCGTCCATG CATGCACTTT AGGTGCAGTG CAGGGCCTCA     900

ACTCGGCCAC GTAGTTAGCG CCACTGCTAC AGATCGAGGC ACCGGTCAGC CGGCCACGCA     960

CGTCGACCGC GCGCGTGCAT TTAAATACGC CGACGACGGA GCTTGATCGA CGAGAGAGCG    1020

AGCGCGATGG GGAGGAGGGC GTGTTGCGCG AAGGAAGGCG TTAAGAGAGG GGCGTGGACG    1080

AGCAAGGAGG ACGATGCCTT GGCCGCCTAC GTCAAGGCCC ATGGCGAAGG CAAATGGAGG    1140

GAAGTGCCCC AGAAAGCCGG TAAAACTAGC TAGTCTTTTT ATTTCATTTT GGGATCATAT    1200

ATATACCCCC GAGGCAAGAC CGGAGGACGA TCACGTGTGT GGGTGCAGGT TTGCGTCGGT    1260

GCGGCAAGAG CTGCCGGCTG CGGTGGCTGA ACTACCTCCG GCCCAACATC AGGCGCGGCA    1320

ACATCTCCTA CGACGAGGAG GATCTCATCA TCCGCCTCCA CAGGCTCCTC GGCAACAGGT    1380

CTGTGCAGTG GCCAGTGGTG GGCTAGCTTA TTACACGAGC TGACGACGAG GCGATCGATC    1440

GAGCGTCTGC TGCGAATTCA TCTGTTCCGG TGTCGGCCGT GTGAGAGTGA GCTCATTCAT    1500
```

-continued

```
ATGTACATGC GTGTTGGCGC GCAGGTGGTC GCTGATTGCA GGCAGGCTGC CTGGCCGAAC     1560

AGACAATGAA ATCAAGAACT ACTGGAACAG CACGCTGGGC CGGAGGGCAG GCGCCGGCGC     1620

CGGCGCCGGC GGCAGCTGGG TCGTCGTCGC GCCGGACACC GGCTCGCACG CCACCCCGGC     1680

CGCGACGTCG GGCGCCTGCG AGACCGGCCA GAATAGCGCC GCTCATCGCG CGGACCCCGA     1740

CTCAGCCGGG ACGACGACGA CCTCGGCGGC GGCGGTGTGG GCGCCCAAGG CCGTGCGGTG     1800

CACGGGCGGA CTCTTCTTCT TCCACCGGGA CACGACGCCG GCGCACGCGG GCGAGACGGC     1860

GACGCCAATG GCCGGTGGAG GTGGAGGAGG AGGAGGAGAA GCAGGGTCGT CGGACGACTG     1920

CAGCTCGGCG GCGTCGGTAT CGCTTCGCGT CGGAAGCCAC GACGAGCCGT GCTTCTCCGG     1980

CGACGGTGAC GGCGACTGGA TGGACGACGT GAGGGCCCTG GCGTCGTTTC TCGAGTCCGA     2040

CGAGGACTGG CTCCGCTGTC AGACGGCCGG GCAGCTTGCG TAGACAACAA GTACACGTAT     2100

AGATGTCCAA TAAGCACGAG GCCCGCGAGC CCGGCACGAA GCCCGCTTTT TGGGCCCGGT     2160

CCGAGCCCGG CACGGCCCGG TTATATGCAG ACCCGGGCCG GCCCGGCACG AATAAGCGGG     2220

CCGGGCTCGG ACAGGAAATT AGGCACGGTG AGCTAGCCCG GCACGGCCCG TTTAGGTCTA     2280

AGCCCGTTAA GCCCGTTTTT TTACACTAAA ACGTGCTTCT CGGCCCGCAT AGCCCGCTTC     2340

TCGGCCCGCT TTTTTCGTGC TAAACGGGCC GGCCCGGCCC GGTTTAGGCC CGTTGCGGGC     2400

CGGGCTCGGA CAGGAAATTG AGCCCGCGTG CTTAGCCGGC CCGGCCCGGT TTTTTAATCG     2460

TGCCTGGCGG GCCAGGCCCA AAACGGGCCG GCTTCACCG GGCCCGGGCC GGACCGGGCC     2520

GGGCGGCCCG TTTGGACATC TCTAAGTACA CGTATGGAGG AGAATATATA TATAGTCATG     2580

CGTACAGCTT GGCGTAATCA TGGTCATAGC TGTTTCCTGT GTGAAATTGT TATCCGCTCA     2640

CAATTCCACA CAACATACGA GCCGGAAGCA TAAAGTGTAA AGCCTGGGGT GCCTAATGAG     2700

TGAGCTAACT CACATTAATT GCGTTGCGCT CACTGCCCGC TTTCCAGTCG GGAAACCTGT     2760

CGTGCCAGCT GCATTAATGA ATCGGCCAAC GCGCGGGGAG AGGCGGTTTG CGTATTGGGC     2820

GCTCTTCCGC TTCCTCGCTC ACTGACTCGC TGCGCTCGGT CGTTCGGCTG CGGCGAGCGG     2880

TATCAGCTCA CTCAAAGGCG GTAATACGGT TATCCACAGA ATCAGGGGAT AACGCAGGAA     2940

AGAACATGTG AGCAAAAGGC CAGCAAAAGG CCAGGAACCG TAAAAAGGCC GCGTTGCTGG     3000

CGTTTTTCCA TAGGCTCCGC CCCCCTGACG AGCATCACAA AAATCGACGC TCAAGTCAGA     3060

GGTGGCGAAA CCCGACAGGA CTATAAAGAT ACCAGGCGTT CCCCCTGGA AGCTCCCTCG     3120

TGCGCTCTCC TGTTCCGACC CTGCCGCTTA CCGGATACCT GTCCGCCTTT CTCCCTTCGG     3180

GAAGCGTGGC GCTTTCTCAA TGCTCACGCT GTAGGTATCT CAGTTCGGTG TAGGTCGTTC     3240

GCTCCAAGCT GGGCTGTGTG CACGAACCCC CCGTTCAGCC CGACCGCTGC GCCTTATCCG     3300

GTAACTATCG TCTTGAGTCC AACCCGGTAA GACACGACTT ATCGCCACTG GCAGCAGCCA     3360

CTGGTAACAG GATTAGCAGA GCGAGGTATG TAGGCGGTGC TACAGAGTTC TTGAAGTGGT     3420

GGCCTAACTA CGGCTACACT AGAAGGACAG TATTTGGTAT CTGCGCTCTG CTGAAGCCAG     3480

TTACCTTCGG AAAAAGAGTT GGTAGCTCTT GATCCGGCAA ACAAACCACC GCTGGTAGCG     3540

GTGGTTTTTT TGTTTGCAAG CAGCAGATTA CGCGCAGAAA AAAGGATCT CAAGAAGATC     3600

CTTTGATCTT TTCTACGGGG TCTGACGCTC AGTGGAACGA AAACTCACGT TAAGGGATTT     3660

TGGTCATGAG ATTATCAAAA AGGATCTTCA CCTAGATCCT TTTAAATTAA AAATGAAGTT     3720

TTAAATCAAT CTAAAGTATA TATGAGTAAA CTTGGTCTGA CAGTTACCAA TGCTTAATCA     3780

GTGAGGCACC TATCTCAGCG ATCTGTCTAT TTCGTTCATC CATAGTTGCC TGACTCCCCG     3840

TCGTGTAGAT AACTACGATA CGGGAGGGCT TACCATCTGG CCCCAGTGCT GCAATGATAC     3900
```

-continued

```
CGCGAGACCC ACGCTCACCG GCTCCAGATT TATCAGCAAT AAACCAGCCA GCCGGAAGGG      3960

CCGAGCGCAG AAGTGGTCCT GCAACTTTAT CCGCCTCCAT CCAGTCTATT AATTGTTGCC      4020

GGGAAGCTAG AGTAAGTAGT TCGCCAGTTA ATAGTTTGCG CAACGTTGTT GCCATTGCTA      4080

CAGGCATCGT GGTGTCACGC TCGTCGTTTG GTATGGCTTC ATTCAGCTCC GGTTCCCAAC      4140

GATCAAGGCG AGTTACATGA TCCCCCATGT TGTGCAAAAA AGCGGTTAGC TCCTTCGGTC      4200

CTCCGATCGT TGTCAGAAGT AAGTTGGCCG CAGTGTTATC ACTCATGGTT ATGGCAGCAC      4260

TGCATAATTC TCTTACTGTC ATGCCATCCG TAAGATGCTT TTCTGTGACT GGTGAGTACT      4320

CAACCAAGTC ATTCTGAGAA TAGTGTATGC GGCGACCGAG TTGCTCTTGC CCGGCGTCAA      4380

TACGGGATAA TACCGCGCCA CATAGCAGAA CTTTAAAAGT GCTCATCATT GGAAAACGTT      4440

CTTCGGGGCG AAAACTCTCA AGGATCTTAC CGCTGTTGAG ATCCAGTTCG ATGTAACCCA      4500

CTCGTGCACC CAACTGATCT TCAGCATCTT TTACTTTCAC CAGCGTTTCT GGGTGAGCAA      4560

AAACAGGAAG GCAAAATGCC GCAAAAAAGG GAATAAGGGC GACACGGAAA TGTTGAATAC      4620

TCATACTCTT CCTTTTTCAA TATTATTGAA GCATTTATCA GGGTTATTGT CTCATGAGCG      4680

GATACATATT TGAATGTATT TAGAAAAATA AACAAATAGG GGTTCCGCGC ACATTTCCCC      4740

GAAAAGTGCC ACCTGACGTC TAAGAAACCA TTATTATCAT GACATTAACC TATAAAAATA      4800

GGCGTATCAC GAGGCCCTTT CGTC                                            4824
```

(2) INFORMATION FOR SEQ ID NO:6:

(i) SEQUENCE CHARACTERISTICS:
        (A) LENGTH: 3915 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: EcoRI-HindIII region of plasmid pCOL13

(ix) FEATURE:
        (A) NAME/KEY: prim_transcript
        (B) LOCATION: 188

(ix) FEATURE:
        (A) NAME/KEY: exon
        (B) LOCATION: 188..212

(ix) FEATURE:
        (A) NAME/KEY: intron
        (B) LOCATION: 213..556

(ix) FEATURE:
        (A) NAME/KEY: exon
        (B) LOCATION: 557..718

(ix) FEATURE:
        (A) NAME/KEY: intron
        (B) LOCATION: 719..1224

(ix) FEATURE:
        (A) NAME/KEY: exon
        (B) LOCATION: 1225..2770

(ix) FEATURE:
        (A) NAME/KEY: CDS
        (B) LOCATION: 576..718

(ix) FEATURE:
        (A) NAME/KEY: CDS
        (B) LOCATION: 1225..2770

(ix) FEATURE:
        (A) NAME/KEY: -

```
      (B) LOCATION: 1268..2770
      (D) OTHER INFORMATION: /note= "3' end of B-peru coding
          region which is derived from cDNA"

(ix) FEATURE:
      (A) NAME/KEY: 3'UTR
      (B) LOCATION: 2771..3272

(ix) FEATURE:
      (A) NAME/KEY: -
      (B) LOCATION: 3273..3891
      (D) OTHER INFORMATION: /label= 3'region
          /note= "further 3' flanking region of B-peru gene.
          This region is only of approximate length and the
          sequence needs to be confirmed."

(ix) FEATURE:
      (A) NAME/KEY: -
      (B) LOCATION: 1..6
      (D) OTHER INFORMATION: /label= EcoRI (ix) FEATURE:
      (A) NAME/KEY: -
      (B) LOCATION: 11..16
      (D) OTHER INFORMATION: /label= XbaI (ix) FEATURE:
      (A) NAME/KEY: -
      (B) LOCATION: 45..50
      (D) OTHER INFORMATION: /label= KpnI (ix) FEATURE:
      (A) NAME/KEY: -
      (B) LOCATION: 265..270
      (D) OTHER INFORMATION: /label= HindIII (ix) FEATURE:
      (A) NAME/KEY: -
      (B) LOCATION: 329..334
      (D) OTHER INFORMATION: /label= XbaI (ix) FEATURE:
      (A) NAME/KEY: -
      (B) LOCATION: 835..840
      (D) OTHER INFORMATION: /label= BamHI (ix) FEATURE:
      (A) NAME/KEY: -
      (B) LOCATION: 1268..1273
      (D) OTHER INFORMATION: /label= MluI (ix) FEATURE:
      (A) NAME/KEY: -
      (B) LOCATION: 2787..2792
      (D) OTHER INFORMATION: /label= HindIII (ix) FEATURE:
      (A) NAME/KEY: -
      (B) LOCATION: 2883..2888
      (D) OTHER INFORMATION: /label= MunI (ix) FEATURE:
      (A) NAME/KEY: -
      (B) LOCATION: 2827..2832
      (D) OTHER INFORMATION: /label= HindIII (ix) FEATURE:
      (A) NAME/KEY: -
      (B) LOCATION: 3892..3897
      (D) OTHER INFORMATION: /label= SalI (ix) FEATURE:
      (A) NAME/KEY: -
      (B) LOCATION: 3910..3915
      (D) OTHER INFORMATION: /label= HindIII (ix) FEATURE:
      (A) NAME/KEY: -
      (B) LOCATION: 3892..3915
      (D) OTHER INFORMATION: /label= polylinker
```

/note= "part of polylinker of pUC19"

(xi) SEQUENCE DESCRIPTION: SEQ ID NO:6:

```
GAATTCAGGT TCTAGACTAT TCTTGTGGCC TCGGGCGGAT GGCGGGTACC CATGTCTTCG      60
TTAGGCTTAT CTGACCGTGG AGATGAAATC TAACGGCTCA TAGAAATTAA ACTAACGTGG     120
ACACTCTGTC CTTGCTGTTT TGCTCCCTGC TCTTTATATA TAGAATGCCT GCTTGCATTG     180
CACCCGTACG TACAGCGTAG CGCGGAGTGG AGGTGAGCTC CTCCTCCGAT TCTTGCCTAA     240
TCTTTGGTCT TTGCACACGT ACGAAAGCTT TTTGCATTGT TTCGTTGCTT CTGGATGATC     300
AGTACTCTTA GATATTAAGC GATACCGATC TAGAATCGAG TTGTTGTACT CTCTCTGTCC     360
CTTTTGTGCA GCTATAACTA GCTAGGTTCC TTCGCATAGA GCCTCTCTAC AGAGTACAGA     420
CTAGCTAGCA GTGTCAGACA CGAAATGGAA ATGGTCACTT CCAAATTGCA CGAGCTGGAA     480
TTATATACTC TTCTGATCTT CTTCACCGTC TCTTTATAGC GTGATATGCG TTTCTGGCTT     540
CTTGCTTACG TGAAGGATTA TTAGTAAGGC GCGTGATGGC GCTCTCAGCT TCCCCGGCTC     600
AGGAAGAACT GCTGCAGCCT GCTGGGAGGC CGTTGAGGAA GCAGCTTGCT GCAGCCGCGA     660
GGAGCATCAA CTGGAGCTAT GCCCTCTTCT GGTCCATTTC AAGCACTCAA CGACCTCGGT     720
AAATGGAAGT CCTGATAATC TATAATTTGT CTGGCAGTTT TCTACAACTC TGGTGAATGA     780
TCGTCACTTC GTTTGCCTGA TACATACATA CATACATATG AAATAAAGAA AGTCGGATCC     840
CGTGATGCGA TTGTAGTTAT CGCTTTTCCG CAAAATGGTT GCTTTTTGAA TCTGCATTCG     900
TTTTTTTCCC ACATCTTCTT CCTTCTCGCG AGTAACGACA ACGCCACCCG CGCCGCCTGC     960
CGCCCATCGC CCCGCCTTGG CCGGCGAGAG CCTCAGCCTA TTACACCAGC GGCGACCTCT    1020
TTTCCCCTTC CTCTCACCGC CCTCGTGGCC GTGCTCTCCC CCGCTCTAAC CTGGTCTGGC    1080
CGCCTCCGCT GCCACCTGCT CCGGCGGCCT CACCCGCGTC TTTCTCGTCC CTACCCTCTC    1140
TGCCTCTGGG CGCATCATCA TCTGATATTC TGATGCAAAT AAAAAGGTA TACCATATAA     1200
GGACAACAGA AAATATGGTT GCAGGGTGCT GACGTGGACG GACGGGTTCT ACAATGGCGA    1260
GGTGAAGACG CGTAAGATCT CCCACTCCGT GGAGCTGACA GCCGACCAGC TGCTCATGCA    1320
GAGGAGCGAG CAGCTCCGGG AGCTCTACGA GGCCCTCCGG TCCGGCGAGT GCGACCGCCG    1380
CGGCGCGCGG CCGGTGGGCT CGCTGTCGCC GGAGGACCTC GGGGACACCG AGTGGTACTA    1440
CGTGATCTGC ATGACCTACG CCTTCCTGCC GGGCCAAGGC TTGCCCGGCA GGAGTTCCGC    1500
GAGCAACGAG CATGTCTGGC TGTGCAACGC GCACCTCGCC GGCAGCAAGG ACTTCCCCCG    1560
CGCGCTCCTG GCCAAGAGCG CGTCCATTCA GACAATCGTC TGCATCCCGC TCATGGGTGG    1620
CGTGCTTGAG CTTGGTACTA CTGATAAGGT GCCGGAGGAC CCGGACTTGG TCAGCCGAGC    1680
AACCGTAGCA TTCTGGGAGC CGCAATGTCC GACATACTCG AAAGAGCCGA GCTCCAACCC    1740
GTCAGCATAC GAAACCGGGG AAGCCGCATA CATAGTCGTG TTGGAGGACC TCGATCACAA    1800
TGCCATGGAC ATGGAGACGG TGACTGCCGC CGCCGGGAGA CACGGAACCG GACAGGAGCT    1860
AGGAGAAGTC GAGAGCCCGT CAAATGCAAG CCTGGAGCAC ATCACCAAGG GGATCGACGA    1920
GTTCTACAGC CTCTGCGAGG AAATGGACGT GCAGCCGCTA GAGGATGCCT GGATAATGGA    1980
CGGGTCTAAT TTCGAAGTCC CGTCGTCAGC GCTCCCGGTG GATGGCTCAA GCGCACCCGC    2040
TGATGGTTCT CGCGCGACAA GTTTCGTGGT TTGGACGAGG TCATCGCACT CCTGCTCGGG    2100
TGAAGCGGCG GTGCCGGTCA TCGAAGAGCC GCAGAAATTG CTGAAGAAAG CGTTGGCCGG    2160
CGGCGGTGCT TGGGCGAACA CGAACTGCGG TGGCGGGGGC ACGACGGTAA CAGCCCAGGA    2220
AAACGGCGCC AAGAACCACG TCATGTCAGA GCGAAAGCGC CGGGAGAAGC TCAACGAGAT    2280
```

```
GTTCTTCGTT CTCAAGTCGT TGGTTCCCTC CATTCACAAG GTGGACAAAG CATCCATCCT    2340

CGCCGAAACG ATAGCCTATC TAAAGGAGCT TCAACGAAGG GTACAAGAAC TGGAATCCAG    2400

GAGGCAAGGT GGCAGTGGGT GTGTCAGCAA GAAAGTCTGT GTGGGCTCCA ACTCCAAGAG    2460

GAAGAGCCCA GAGTTCGCCG GTGGCGCGAA GGAGCACCCC TGGGTCCTCC CCATGGACGG    2520

CACCAGCAAC GTCACCGTCA CCGTCTCGGA CACGAACGTG CTCCTGGAGG TGCAATGCCG    2580

GTGGGAGAAG CTCCTGATGA CACGGGTGTT CGACGCCATC AAGAGCCTCC ATTTGGACGC    2640

TCTCTCGGTT CAGGCTTCGG CACCAGATGG CTTCATGAGG CTCAAGATAG GAGCTCAGTT    2700

TGCAGGCTCC GGCGCCGTCG TGCCCGGAAT GATCAGCCAA TCTCTTCGTA AAGCTATAGG    2760

GAAGCGATGA AAGGGCGCTA CATGTGAAGC TTAATTAATG GAAGCAAACT TGTATTTCTT    2820

GTGCAAAAGC TTACTATATA TTTCTGCAAA ACCTGGTGTG CCTTGTTTTG ATTTTCAGTC    2880

GCCAATTGTG CCTTTGTTTT TATCAAGTGA TGATCTACAC ATATATATAG GAATATTTGA    2940

AAAGAGCGAT GTCATAGGGT TTTTTTATTA CAAGGAACAA GTCTTTCACG TGCTGGCCTC    3000

ACAAATCCTA AGAGAAAATC TGCTCATTTT GATTGCGTTC CGCAACAACT CTGTAATCCA    3060

TATCCTATGT ATCCGATCAA CTAGTCGATA GCCTCCGTCC GCCACATCAT CATATATCTA    3120

TCTATGTGTG TCATCTGACA CATACTCCTC GCGTACTGTG CTGACATATG ATACTGACAC    3180

AGCATATATG CATGCACATC GTCACACGAC ATATATCTCG CTACTACACA GATATTGGAT    3240

ACGATACTAT ATAGCATCAT GCGTGCTGCG ATNNNNNNNN NNNNNNNNNN NNNNNNNNNN    3300

NNNNNNNNNN NNNNNNNNNN NNNNNNNNNN NNNNNNNNNN NNNNNNNNNN NNNNNNNNNN    3360

NNNNNNNNNN NNNNNNNNNN NNNNNNNNNN NNNNNNNNNN NNNNNNNNNN NNNNNNNNNN    3420

NNNNNNNNNN NNNNNNNNNN NNNNNNNNNN NNNNNNNNNN NNNNNNNNNN NNNNNNNNNN    3480

NNNNNNNNNN NNNNNNNNNN NNNNNNNNNN NNNNNNNNNN NNNNNNNNNN NNNNNNNNNN    3540

NNNNNNNNNN NNNNNNNNNN NNNNNNNNNN NNNNNNNNNN NNNNNNNNNN NNNNNNNNNN    3600

NNNNNNNNNN NNNNNNNNNN NNNNNNNNNN NNNNNNNNNN NNNNNNNNNN NNNNNNNNNN    3660

NNNNNNNNNN NNNNNNNNNN NNNNNNNNNN NNNNNNNNNN NNNNNNNNNN NNNNNNNNNN    3720

NNNNNNNNNN NNNNNNNNNN NNNNNNNNNN NNNNNNNNNN NNNNNNNNNN NNNNNNNNNN    3780

NNNNNNNNNN NNNNNNNNNN NNNNNNNNNN NNNNNNNNNN NNNNNNNNNN NNNNNNNNNN    3840

NNNNNNNNNN NNNNNNNNNN NNNNNNNNNN NNNNNNNNNN NNNNNNNNNN NGTCGACCTG    3900

CAGGCATGCA AGCTT                                                    3915

(2) INFORMATION FOR SEQ ID NO:7:

(i) SEQUENCE CHARACTERISTICS:
          (A) LENGTH: 4137 base pairs
          (B) TYPE: nucleic acid
          (C) STRANDEDNESS: double
          (D) TOPOLOGY: linear (ii) MOLECULE TYPE: DNA (genomic)

(vi) ORIGINAL SOURCE:
          (A) ORGANISM: EcoRI-HindIII region of plasmid pCOL13

(ix) FEATURE:
          (A) NAME/KEY: prim_transcript
          (B) LOCATION: 188

(ix) FEATURE:
          (A) NAME/KEY: exon
          (B) LOCATION: 188..212

(ix) FEATURE:
          (A) NAME/KEY: intron
```

-continued

```
         (B) LOCATION: 213..556

(ix) FEATURE:
         (A) NAME/KEY: exon
         (B) LOCATION: 557..718

(ix) FEATURE:
         (A) NAME/KEY: intron
         (B) LOCATION: 719..1224

(ix) FEATURE:
         (A) NAME/KEY: exon
         (B) LOCATION: 1226..2771
         (D) OTHER INFORMATION: /codon_start= 2
             /note= "exon containing 3' end coding region
             of B-peru gene. This exon continues up to the
             polyadenylation site."

(ix) FEATURE:
         (A) NAME/KEY: CDS
         (B) LOCATION: 576..718

(ix) FEATURE:
         (A) NAME/KEY: CDS
         (B) LOCATION: 1226..2771

(ix) FEATURE:
         (A) NAME/KEY: -
         (B) LOCATION: 1269..2771
         (D) OTHER INFORMATION: /note= "fragment of B-peru coding
             region which is derived from cDNA"

(ix) FEATURE:
         (A) NAME/KEY: 3'UTR
         (B) LOCATION: 2772..4137

(ix) FEATURE:
         (A) NAME/KEY: -
         (B) LOCATION: 1..6
         (D) OTHER INFORMATION: /label= EcoRI (ix) FEATURE:
         (A) NAME/KEY: -
         (B) LOCATION: 11..16
         (D) OTHER INFORMATION: /label= XbaI (ix) FEATURE:
         (A) NAME/KEY: -
         (B) LOCATION: 45..50
         (D) OTHER INFORMATION: /label= KpnI (ix) FEATURE:
         (A) NAME/KEY: -
         (B) LOCATION: 265..270
         (D) OTHER INFORMATION: /label= HindIII (ix) FEATURE:
         (A) NAME/KEY: -
         (B) LOCATION: 329..334
         (D) OTHER INFORMATION: /label= XbaI (ix) FEATURE:
         (A) NAME/KEY: -
         (B) LOCATION: 835..840
         (D) OTHER INFORMATION: /label= BamHI (ix) FEATURE:
         (A) NAME/KEY: -
         (B) LOCATION: 1269..1274
         (D) OTHER INFORMATION: /label= MluI (ix) FEATURE:
         (A) NAME/KEY: -
         (B) LOCATION: 2788..2793
         (D) OTHER INFORMATION: /label= HindIII (ix) FEATURE:
         (A) NAME/KEY: -
         (B) LOCATION: 2884..2889
         (D) OTHER INFORMATION: /label= MunI
```

(ix) FEATURE:
    (A) NAME/KEY: -
    (B) LOCATION: 2828..2833
    (D) OTHER INFORMATION: /label= HindIII (ix) FEATURE:
    (A) NAME/KEY: -
    (B) LOCATION: 4114..4119
    (D) OTHER INFORMATION: /label= SalI (ix) FEATURE:
    (A) NAME/KEY: -
    (B) LOCATION: 4132..4137
    (D) OTHER INFORMATION: /label= HindIII (ix) FEATURE:
    (A) NAME/KEY: -
    (B) LOCATION: 4114..4137
    (D) OTHER INFORMATION: /label= polylinker
        /note= "part of polylinker of pUC19"

(xi) SEQUENCE DESCRIPTION: SEQ ID NO:7:

```
GAATTCAGGT TCTAGACTAT TCTTGTGGCC TCGGGCGGAT GGCGGGTACC CATGTCTTCG      60
TTAGGCTTAT CTGACCGTGG AGATGAAATC TAACGGCTCA TAGAAATTAA ACTAACGTGG     120
ACACTCTGTC CTTGCTGTTT TGCTCCCTGC TCTTTATATA TAGAATGCCT GCTTGCATTG     180
CACCCGTACG TACAGCGTAG CGCGGAGTGG AGGTGAGCTC CTCCTCCGAT TCTTGCCTAA     240
TCTTTGGTCT TTGCACACGT ACGAAAGCTT TTTGCATTGT TTCGTTGCTT CTGGATGATC     300
AGTACTCTTA GATATTAAGC GATACCGATC TAGAATCGAG TTGTTGTACT CTCTCTGTCC     360
CTTTTGTGCA GCTATAACTA GCTAGGTTCC TTCGCATAGA GCCTCTCTAC AGAGTACAGA     420
CTAGCTAGCA GTGTCAGACA CGAAATGGAA ATGGTCACTT CCAAATTGCA CGAGCTGGAA     480
TTATATACTC TTCTGATCTT CTTCACCGTC TCTTTATAGC GTGATATGCG TTTCTGGCTT     540
CTTGCTTACG TGAAGGATTA TTAGTAAGGC GCGTGATGGC GCTCTCAGCT TCCCCGGCTC     600
AGGAAGAACT GCTGCAGCCT GCTGGGAGGC CGTTGAGGAA GCAGCTTGCT GCAGCCGCGA     660
GGAGCATCAA CTGGAGCTAT GCCCTCTTCT GGTCCATTTC AAGCACTCAA CGACCTCGGT     720
AAATGGAAGT CCTGATAATC TATAATTTGT CTGGCAGTTT TCTACAACTC TGGTGAATGA     780
TCGTCACTTC GTTTGCCTGA TACATACATA CATACATATG AAATAAAGAA AGTCGGATCC     840
CGTGATGCGA TTGTAGTTAT CGCTTTTCCG CAAAATGGTT GCTTTTTGAA TCTGCATTCG     900
TTTTTTTCCC ACATCTTCTT CCTTCTCGCG AGTAACGACA ACGCCACCGC GCGCCGCCTG     960
CCGCCCATCG CCCCGCCTTG GCCGGCGAGA GCCTCAGCCT ATTACACCAG CGGCGACCTC    1020
TTTTCCCCTT CCTCTCACCG CCCTCGTGGC CGTGCTCACC CCCGCTCTAA CCTGGTCTGG    1080
CCGCCTCCGC TGCCACCTGC TCCGGCGGCC TCACCCGCGT CTTTCTCGTC CCTACCCTCT    1140
CTGCCTCTGG GCGCATCATC ATCTGATATT CTGATGCAAA GAAAAAAGGT ATACCATATA    1200
AGGACAACAG AAAATATGGT TGCAGGGTGC TGACGTGGAC GGACGGGTTC TACAATGGCG    1260
AGGTGAAGAC GCGTAAGATC TCCCACTCCG TGGAGCTGAC AGCCGACCAG CTGCTCATGC    1320
AGAGGAGCGA GCAGCTCCGG GAGCTCTACG AGGCCCTCCG GTCCGGCGAG TGCGACCGCC    1380
GCGGCGCGCG GCCGGTGGGC TCGCTGTCGC CGGAGGACCT CGGGGACACC GAGTGGTACT    1440
ACGTGATCTG CATGACCTAC GCCTTCCTGC CGGGCCAAGG CTTGCCCGGC AGGAGTTCCG    1500
CGAGCAACGA GCATGTCTGG CTGTGCAACG CGCACCTCGC CGGCAGCAAG GACTTCCCCC    1560
GCGCGCTCCT GGCCAAGAGC GCGTCCATTC AGACAATCGT CTGCATCCCG CTCATGGGTG    1620
GCGTGCTTGA GCTTGGTACT ACTGATAAGG TGCCGGAGGA CCCGGACTTG GTCAGCCGAG    1680
```

```
CAACCGTAGC ATTCTGGGAG CCGCAATGTC CGACATACTC GAAAGAGCCG AGCTCCAACC    1740

CGTCAGCATA CGAAACCGGG GAAGCCGCAT ACATAGTCGT GTTGGAGGAC CTCGATCACA    1800

ATGCCATGGA CATGGAGACG GTGACTGCCG CCGCCGGGAG ACACGGAACC GGACAGGAGC    1860

TAGGAGAAGT CGAGAGCCCG TCAAATGCAA GCCTGGAGCA CATCACCAAG GGGATCGACG    1920

AGTTCTACAG CCTCTGCGAG GAAATGGACG TGCAGCCGCT AGAGGATGCC TGGATAATGG    1980

ACGGGTCTAA TTTCGAAGTC CCGTCGTCAG CGCTCCCGGT GGATGGCTCA AGCGCACCCG    2040

CTGATGGTTC TCGCGCGACA AGTTTCGTGG TTTGGACGAG GTCATCGCAC TCCTGCTCGG    2100

GTGAAGCGGC GGTGCCGGTC ATCGAAGAGC CGCAGAAATT GCTGAAGAAA GCGTTGGCCG    2160

GCGGCGGTGC TTGGGCGAAC ACGAACTGCG GTGGCGGGGG CACGACGGTA ACAGCCCAGG    2220

AAAACGGCGC CAAGAACCAC GTCATGTCAG AGCGAAAGCG CCGGGAGAAG CTCAACGAGA    2280

TGTTCCTCGT TCTCAAGTCG TTGGTTCCCT CCATTCACAA GGTGGACAAA GCATCCATCC    2340

TCGCCGAAAC GATAGCCTAT CTAAAGGAGC TTCAACGAAG GGTACAAGAA CTGGAATCCA    2400

GGAGGCAAGG TGGCAGTGGG TGTGTCAGCA AGAAAGTCTG TGTGGGCTCC AACTCCAAGA    2460

GGAAGAGCCC AGAGTTCGCC GGTGGCGCGA AGGAGCACCC CTGGGTCCTC CCCATGGACG    2520

GCACCAGCAA CGTCACCGTC ACCGTCTCGG ACACGAACGT GCTCCTGGAG GTGCAATGCC    2580

GGTGGGAGAA GCTCCTGATG ACACGGGTGT TCGACGCCAT CAAGAGCCTC CATTTGGACG    2640

CTCTCTCGGT TCAGGCTTCG GCACCAGATG GCTTCATGAG GCTCAAGATA GGAGCTCAGT    2700

TTGCAGGCTC CGGCGCCGTC GTGCCCGGAA TGATCAGCCA ATCTCTTCGT AAAGCTATAG    2760

GGAAGCGATG AAAGGGCGCT ACATGTGAAG CTTAATTAAT GGAAGCAAAC TTGTATTTCT    2820

TGTGCAAAAG CTTACTATAT ATTTCTGCAA AACCTGGTGT GCCTTGTTTT GATTTTCAGT    2880

CGCCAATTGT GCCTTTGTTT TTATCAAGTG ATGATCTACA CTATATATAT GGAATATTTG    2940

AAAAGAGCGA TGTCATAGGG TTTTTTTATT ACAAGGAACA AGTCTTTCAC GTGCTGGCCT    3000

CACAAATCCA AGAGAAAATC TGCTCATTTT GATTGGCTTC CGCAACAACT CTGTAATCCA    3060

TATCCTTTGT ATCCGATCAA CTATGATACC TCCTCCCCCA TCTCTTTTTT TTTTATCTGC    3120

ACAATCTTCT ATTCTACTAT AATGAAACAA TAGAGCCACT ACCGAATATT TCCTCAAAAA    3180

TGTACAACAA ACTAGGGTGG TCCAAACAAA TGCCTAGAGG AGCTAGATTC TCTTAAATTA    3240

GACATCGGTT TCTTTTATCT CTTCCAGAAG GGATAAAAGT ATGTGTTTAT GGTCTTCAGT    3300

AATACATTGT TCGTTTCTCA TAGTCAATTT AGAGGTGTTT AAATGTACTT GAACTAATAG    3360

TTAGTTGGTT TAAAAATTAC TATTAAAATT AGTTAGTTAA TAAATAGCTA GCTAAATATT    3420

AGCTAATTTG TCAAAAGTAG CTAATAGCTG AATTATTAGC TATATTGTTT TGATGTCTTC    3480

AGCTAATTTT AGCAGATCAT TATTAGTTCT AGTGTATCTA AACACACCCT TAGTCAAACA    3540

TGGTAAAAAA AAAGTTGATT CACTCATTGC TCATCGAAGA CGCAGATCAT GGCATCCCTC    3600

ACACGTTCTT CAGCCTACAC GGCACTTGCA TTGTAATTGC ATCTCATCTC ATCAACCCTT    3660

GTTGTGCATT ACTTGCCACA TGCGCCATCA ATTAACATTT TTTTGTCTCG TTCCTGAATT    3720

TCCTAACAAA TTTCATCAAA TGTACGCAGA GCTAAAGCTA GCTGTCGATG TCAGTTGACA    3780

GTTGACACCG ATGAATTTTA GAAAATTTAG TGTAAAGTAC TATTTATAAT GTTCATGACA    3840

CCCATATAAA ATATGTTGAC ACCGGCAAAC CTCAAGGCTA GCTTCGCCCC TGCCATCAAC    3900

CTTACATCTA CATTCACCAC GAGGTGTGCA CGGCCTAGGT TCGACTCCTA TGTCATGCCT    3960

TGCTATCTAC AGATTCAGCA AGTGTTGTGT TCCTTGTTGT CACAATCTAC CTTTATTATA    4020

AAATTGATGT CATATCATGC CAAACAACAA ATAATTAATA TCGTGTGAAA TTTGAATTTC    4080
```

```
TCTAACATGC TCAACCAACC TTACCCCTTC ACGGTCGACC TGCAGGCATG CAAGCTT        4137
```

(2) INFORMATION FOR SEQ ID NO:8:

(i) SEQUENCE CHARACTERISTICS:
        (A) LENGTH: 2662 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

```
ACTAGTACCT GTCGCGCGCC CATGCGCGCG TGGCGTGCTT CTCGCCCTGG TAACTGTTCT          60
CGGCAAATGA CTATTTCCAA GTAAACATAT TCAATGATTT TGCTATTCTT AGCAAAGTAA         120
TTTCACTTGG ACTTTTGTGC CAAAAACGCA TTGGAAAAAA TCTCCTTGGA CTCCAGCCTA         180
AGGTTGAAAG TGTAAAAACT GGGAAAAATT ATTGATGTTT CGGGCAGTTA CTTGGCTATG         240
TAAATTCCAT ACCTTTTCAA AATATCCTAA ACATTCTTTT CTGTTTCTGC AACATACATG         300
TTTATCAGTT CTGGACCTTT GACGCTACGA AAGTTCAGTG AGTATTCAGG CTTTCGCAAG         360
TAAAACCTAG AAGTCCAACG GACATTCATT TTAGCGATTC CATGTCTTTA GGATGCACTT         420
GTTATCGGAT GTCTCCTATG AGACAGAATG CACTTGTTAT GGTAACTAAA CAAAAAAATA         480
TAATTTAATT CGTGTGAAAC TTTTTCAAAC CTACCTTCCC TGTTCCCGGA GGTCCATATA         540
CCCAGACACC TAATCGCTTG CGCAATTTAG AAGAAATCAT GCGATTATAC GTCAAAGGGA         600
GCTGAAATAT CAAGCAAAAG AAAAGGTCAT CCCACAAAAG CCCAAAACTA TTGTAGGGAA         660
AACACTTGTT TTACCTATAA TTGAGCGTCG TATTGGTGTT GCTGATATTT ACTGCTAAAC         720
CAAGTCCAAT TTACCAGAAT AGTATCTAGA AGAATCCTTT TCACATCCTC TAGCCCGCCA         780
ACATCCTACC ATTTGACATT GAGAACTAAA AAACAAATTG TTCCCAGACG AAAGCTAAAG         840
TCGCTTTATA CGATTAGCTG CAGTAGGTGA GCACGATCTC CGAACGCTGG GCATGACACG         900
ACCATGATAG ACGACATGGA CATTTTGTCA AACACCTGCA TGGCGTCACC AGGGAAAACA         960
ATCCAGCAGG AGAGTTGGGA GAGAGATGGA AACAATTAAT TATGCAAACA CGGAGGAGAC        1020
ACAATTTGAA GAGTGTTCGT ACACCTACGG CAATCAGCGA AACGATGAGA GAGCATACCA        1080
AGCTCGGGTC GTCAGACACG CGGAGGACGG ACGGTGGCAC CGATGGAGAT GGAGACAGTT        1140
GCGTGCCGTT TTTTGTGGAG GGCTTCGTTG GTGTCGGGCG TCGGCGGACC CTGAACGCGG        1200
TGGGAAGAAG AGCGGCGTGG TGGGAAGAAG AGCGACGTCA GGTTCTAGAC TATTCTTGTG        1260
GCCTCGGGCG GATGGCGGGT ACCCATGTCT TCGTTAGGCT TATCTGACCG TGGAGATGAA        1320
ATCTAACGGC TCATAGAAAT TAAACTAACG TGGACTCCCA GACGAAAGCT AAAGTCGCTT        1380
TATACGATTA GCTGCAGTAG GTGAGCACGA TCTCCGAACG CTGGGCATGA CACGACCATG        1440
ATAGACGACA TGGACATTTT GTCAAACACC TGCATGGCGT CACCAGGGAA ACAATCCAG         1500
CAGGAGAGTT GGGAGAGAGA TGGAAACAAT TAATTATGCA AACACGGAGG AGACACAATT        1560
TGAAGAGTGT TCGTACACCT ACGGCAATCA GCGAAACGAT GAGAGAGCAT ACCAAGCTCG        1620
GGTCGTCAGC AACGCGGAGG ACGGACGGTG GCACCGATGG AGATGGAGAC AGTTGCGTGC        1680
CGTTTTTTGT GGAGGGCTTC GTTGGTGTCG GCGTCGGCG GAGCCTGAAC GCGGTGGGAA         1740
GAAGAGCTTC GTGGTGGGAA GAAGAGCGAC GACAGGTTCT AGACTATTCT TGTGGCCTCG        1800
GGCGGATGGC GGGTACCCAT GTCTTCGTTA GGCTTATCTG ACCGTGGAGA TGAAATCTAA        1860
CGGCTCATAG AAATTAAACT AACGTGGACA CTCTGTCCTT GCTGTTTTGC TCCCTGCTCT        1920
TTATATATAG AATGCCTGCT TGCATTGCAC CCGTACGTAC AGCGTAGCGC GGAGTGGAGG        1980
```

```
TGAGCTCCTC CTCCGATTCT TGCCTAATCT TTGGTCTTTG CACACGTACG AAAGCTTTTT      2040

GCATTGTTTC GTTGCTTCTG GATGATCAGT ACTCTTAGAT ATTAAGCGAT ACCGATCTAG      2100

AATCGAGTTG TTGTACTCTC TCTGTCCCTT TTGTGCAGCT ATAACTAGCT AGGTTCCTTC      2160

GCATAGAGCC TCTCTACAGA GTACAGACTA GCTAGCAGTG TCAGACACGA AATGGAAATG      2220

GTCACTTCCA AATTGCACGA GCTGGAATTA TATACTCTTC TGATCTTCTT CACCGTCTCT      2280

TTATAGCGTG ATATGCGTTT CTGGCTTCTT GCTTACGTGA AGGATTATTA GTAAGGCGCG      2340

TGATGGCGCT CTCAGCTTCC CCGGCTCAGG AAGAACTGCT GCAGCCTGCT GGGAGGCCGT      2400

TGAGGAGGCA GCTTGCTGCA GCCGCGAGGA GCATCAACTG GAGCTATGCC CTCTTCTGGT      2460

CCATTTCAAG CACTCAACGA CCTCGGTAAA TGGAAGTCCT GATAATCTAT AATTTGTCTG      2520

GCAGTTTTCT ACAACTCTGG TGAATGATCG TCACTTCGTT TGCCTGATAC ATACATACAT      2580

ACATATGAAA TAAAGAAAGT CGGATCCCGT GATGCGATTG TAGTTATCGC TTTTCCGCAA      2640

AATGGTTGCT TTTTGAATCT GC                                              2662
```